US012395329B1

(12) United States Patent
Pasquali et al.

(10) Patent No.: US 12,395,329 B1
(45) Date of Patent: Aug. 19, 2025

(54) RECORD-LEVEL ENCRYPTION SCHEME FOR DATA OWNERSHIP PLATFORM

(71) Applicant: Ecosteer Srl, Bolzano (IT)

(72) Inventors: Elena Pasquali, Bolzano (IT); Daniele Grazioli, Bolzano (IT); Gabriele Sankalaite, Padua (IT); Georgiana Bud, Bolzano (IT)

(73) Assignee: Ecosteer Srl (IT)

( * ) Notice: Subject to any disclaimer, the term of this patent is extended or adjusted under 35 U.S.C. 154(b) by 0 days.

(21) Appl. No.: 18/759,426

(22) Filed: Jun. 28, 2024

(51) Int. Cl.
*H04L 9/08* (2006.01)
(52) U.S. Cl.
CPC .................................. *H04L 9/088* (2013.01)
(58) Field of Classification Search
None
See application file for complete search history.

(56) References Cited

U.S. PATENT DOCUMENTS

| | | | | |
|---|---|---|---|---|
| 7,146,495 B2 * | 12/2006 | Baldwin | ............... | H04L 9/0894 713/168 |
| 8,837,725 B2 * | 9/2014 | Teruyama | ............. | H04L 9/3236 380/255 |
| 9,342,699 B2 * | 5/2016 | Bowman | ............ | G11B 20/0021 |
| 9,443,097 B2 * | 9/2016 | O'Hare | ............... | G06F 11/1076 |
| 9,646,172 B1 * | 5/2017 | Hahn | .................... | G06F 21/602 |
| 10,038,677 B1 * | 7/2018 | Howell | ................. | H04L 9/3236 |
| 10,783,269 B1 * | 9/2020 | Shraer | ................. | H04L 67/1097 |
| 10,867,057 B1 * | 12/2020 | Knas | ....................... | G06F 21/32 |
| 11,258,601 B1 * | 2/2022 | Wang | ...................... | H04L 9/088 |
| 11,528,131 B1 * | 12/2022 | Valkaitis | ............... | H04L 9/0822 |
| 11,582,028 B1 * | 2/2023 | Valkaitis | ............... | H04L 9/0825 |
| 11,595,205 B1 * | 2/2023 | Sosothikul | .......... | G06F 11/1469 |
| 11,646,869 B1 * | 5/2023 | Tamosiunas | .......... | H04L 9/0819 713/171 |
| 11,671,247 B2 * | 6/2023 | Racz | ................ | G08B 13/19667 713/171 |
| 11,671,251 B1 * | 6/2023 | Copparapu | ........... | H04L 9/0825 380/44 |
| 11,765,170 B2 * | 9/2023 | Zhou | ................... | H04L 63/0428 713/171 |
| 11,777,913 B2 * | 10/2023 | Shockley | ............. | H04L 9/3247 713/171 |

(Continued)

*Primary Examiner* — Kambiz Zand
*Assistant Examiner* — Mahabub S Ahmed
(74) *Attorney, Agent, or Firm* — Sterne, Kessler, Goldstein & Fox P.L.L.C.

(57) ABSTRACT

Disclosed herein are embodiments for a record-level encryption scheme. A data visibility control platform may facilitate record-level encryption between a data owner device and a requester device, requesting access to the encrypted record. The record may contain sensitive and/or confidential information of the data owner. The data owner may directly control the visibility of the record via the data visibility control platform. The data visibility control platform may use a combination of private and public cryptographic keys associated with the data owner and requester to provide record-level encryption. An embodiment may include record keys used to encrypt records being stored by a records database managed by a data intermediary. The record key may be encrypted using the public key of the data owner and stored on a blockchain. Access to the record key stored on the blockchain is controlled by the data owner.

24 Claims, 15 Drawing Sheets

(56) References Cited

U.S. PATENT DOCUMENTS

| | | | |
|---|---|---|---|
| 11,790,113 B2* | 10/2023 | Gonzalez Cervantes | G06F 21/6245 713/171 |
| 11,860,673 B1* | 1/2024 | Kodakandla | H04L 9/0822 |
| 11,902,427 B2* | 2/2024 | Valkaitis | H04L 9/088 |
| 2004/0098579 A1* | 5/2004 | Nakano | G06F 21/10 713/150 |
| 2009/0316897 A1* | 12/2009 | Kambayashi | H04L 9/0897 380/255 |
| 2009/0323972 A1* | 12/2009 | Kohno | G06F 21/6245 380/284 |
| 2010/0161989 A1* | 6/2010 | Kosaki | H04L 63/061 380/259 |
| 2010/0179831 A1* | 7/2010 | Brown | G16Z 99/00 713/170 |
| 2011/0004555 A1* | 1/2011 | Onda | G06F 21/10 713/150 |
| 2012/0204032 A1* | 8/2012 | Wilkins | H04L 9/321 713/170 |
| 2013/0159193 A1* | 6/2013 | Tang | G06Q 20/1235 705/51 |
| 2013/0183934 A1* | 7/2013 | Roemer | H04W 8/265 455/411 |
| 2013/0212704 A1* | 8/2013 | Shablygin | G06F 21/6218 726/28 |
| 2014/0201084 A1* | 7/2014 | Dagenais | G06Q 20/382 705/64 |
| 2014/0325229 A1* | 10/2014 | Bacastow | G06F 11/1458 726/4 |
| 2015/0019870 A1* | 1/2015 | Patnala | H04L 9/0822 713/171 |
| 2015/0089590 A1* | 3/2015 | Krishnan | A61N 1/37254 607/59 |
| 2015/0304306 A1* | 10/2015 | Ponsford | H04L 63/045 713/193 |
| 2017/0351871 A1* | 12/2017 | Christiansen | G06F 21/78 |
| 2018/0227120 A1* | 8/2018 | Takemori | G06F 21/44 |
| 2019/0116030 A1* | 4/2019 | Wiacek | H04L 9/0861 |
| 2019/0190703 A1* | 6/2019 | Lekkas | H04L 9/0825 |
| 2019/0245682 A1* | 8/2019 | Alwen | H04L 9/3247 |
| 2019/0347433 A1* | 11/2019 | Chakravorty | H04L 9/30 |
| 2020/0036519 A1* | 1/2020 | Bitauld | H04L 9/0897 |
| 2020/0145199 A1* | 5/2020 | Kounavis | G06F 12/1408 |
| 2020/0145200 A1* | 5/2020 | Le Van Gong | H04L 9/30 |
| 2020/0193033 A1* | 6/2020 | Kurmi | H04L 9/0894 |
| 2021/0036869 A1* | 2/2021 | Don | H04L 9/3263 |
| 2021/0091946 A1* | 3/2021 | Yoshida | H04L 9/16 |
| 2021/0119793 A1* | 4/2021 | Gaddam | H04L 9/0861 |
| 2021/0167954 A1* | 6/2021 | Weiss | H04L 9/0825 |
| 2021/0234845 A1* | 7/2021 | Smelov | H04L 51/046 |
| 2021/0320786 A1* | 10/2021 | Simpson | G06F 21/608 |
| 2021/0344484 A1* | 11/2021 | Pasquali | H04L 65/80 |
| 2021/0344685 A1* | 11/2021 | Gous | H04W 12/084 |
| 2021/0377001 A1* | 12/2021 | Schrage | H04L 9/3239 |
| 2022/0060323 A1* | 2/2022 | Payne | H04L 9/0897 |
| 2022/0083511 A1* | 3/2022 | Hornquist Astrand | H04L 9/3247 |
| 2022/0237595 A1* | 7/2022 | Roach | H04L 9/0822 |
| 2022/0239480 A1* | 7/2022 | Hetzler | H04L 9/0891 |
| 2022/0284087 A1* | 9/2022 | Hunt | H04L 9/3242 |
| 2022/0300435 A1* | 9/2022 | Bretfeld | G06F 12/1433 |
| 2023/0085843 A1* | 3/2023 | Valkaitis | G06F 3/062 713/165 |
| 2023/0086968 A1* | 3/2023 | Valkaitis | H04L 9/085 713/171 |
| 2023/0179404 A1* | 6/2023 | Jwa | H04L 9/0825 713/171 |
| 2023/0246821 A1* | 8/2023 | Bursell | H04L 9/0825 713/171 |
| 2023/0283455 A1* | 9/2023 | Shaffer | H04L 9/0819 713/171 |
| 2023/0283463 A1* | 9/2023 | Shaffer | H04L 9/30 713/171 |
| 2023/0291565 A1* | 9/2023 | Ureche | H04L 9/0825 |
| 2024/0028455 A1* | 1/2024 | Horan | G06F 3/0622 |
| 2024/0160753 A1* | 5/2024 | Niemelä | H04L 9/50 |
| 2024/0187225 A1* | 6/2024 | Yang | G06F 21/10 |
| 2024/0235829 A1* | 7/2024 | Jeong | H04L 9/30 |
| 2024/0250807 A1* | 7/2024 | Kazlauskas | H04L 9/0825 |
| 2024/0275588 A1* | 8/2024 | Lee | H04L 9/0894 |

* cited by examiner

| Transaction ID 260.1 | Cryptographic Hash 222.1 | Encrypted Record Key 240B.1 | Key Identifier 224.1 |
| --- | --- | --- | --- |
| Transaction ID 260.2 | Cryptographic Hash 222.2 | Encrypted Record Key 240B.2 | Key Identifier 224.2 |
| Transaction ID 260.3 | Cryptographic Hash 222.3 | Encrypted Record Key 240B.3 | Key Identifier 224.3 |
| Transaction ID 260.4 | Cryptographic Hash 222.4 | Encrypted Record Key 240B.4 | Key Identifier 224.4 |
| Transaction ID 260.5 | Cryptographic Hash 222.5 | Encrypted Record Key 240B.5 | Key Identifier 224.5 |

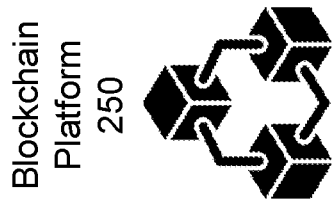

Blockchain Platform 250

FIG. 3A

| Transaction ID 260.1 | Encrypted Record 220C.1 | Cryptographic Hash 222.1 |
| Transaction ID 260.2 | Encrypted Record 220C.2 | Cryptographic Hash 222.2 |
| Transaction ID 260.3 | Encrypted Record 220C.3 | Cryptographic Hash 222.3 |
| Transaction ID 260.4 | Encrypted Record 220C.4 | Cryptographic Hash 222.4 |
| Transaction ID 260.5 | Encrypted Record 220C.5 | Cryptographic Hash 222.5 |

Data Intermediary 150

RECORD-LEVEL ENCRYPTION SCHEME FOR DATA OWNERSHIP PLATFORM

BACKGROUND

Field

The disclosed technology is generally related to systems and methods for a record-level encryption scheme for a data ownership platform.

Related Art

Consent management and data visibility are continuing issues as entities continue to electronically store and share data. Consent management may include access controls, e.g., enforcement of security protocols, as well as liability, e.g., liability for data breaches. Data visibility may include management of individuals and entities able to view, read, write, and edit stored data. In current systems, data consent management and visibility are centralized such that a data intermediary may manage both consent and visibility of the data of data owners for both data owners and data users.

In the healthcare industry, there have been efforts to allow patients to control their clinical data that have focused on the development of patient-managed records, or Personal Health Records (PHRs). These solutions, however, have significant shortcomings, such as placing significant administrative and security burdens on patients. Other known solutions for managing patient health records place control of record access with Data Intermediation Services Providers, and are used in combination with centralized clinical data repositories often referred to as Electronic Health Records (EHRs). EHRs offer certain advantages over PHRs, such as comprehensive health data, potential interoperability across systems, adherence to security and compliance standards, integration with clinical workflows, support for population health management, and facilitation of provider-to-provider communication. A clear disadvantage of current records access control methods applied to EHRs, however, is that patients do not control who has access to and visibility over their own data. The Data Intermediation Services Providers have both control over EHRs access and over the visibility of records maintained in the EHR. Currently, there is no solution that enables patients to control dissemination and use of their sensitive data while leveraging certain advantages that are associated with centralized data repositories such as EHRs.

BRIEF DESCRIPTION OF THE DRAWINGS

The accompanying drawings are incorporated herein and form a part of the specification.

FIG. 3A depicts an example record stored on a blockchain, according to some embodiments.

In the drawings, like reference numbers generally indicate identical or similar elements. Additionally, generally, the left-most digit(s) of a reference number identifies the drawing in which the reference number first appears.

DETAILED DESCRIPTION

Figure 1A:
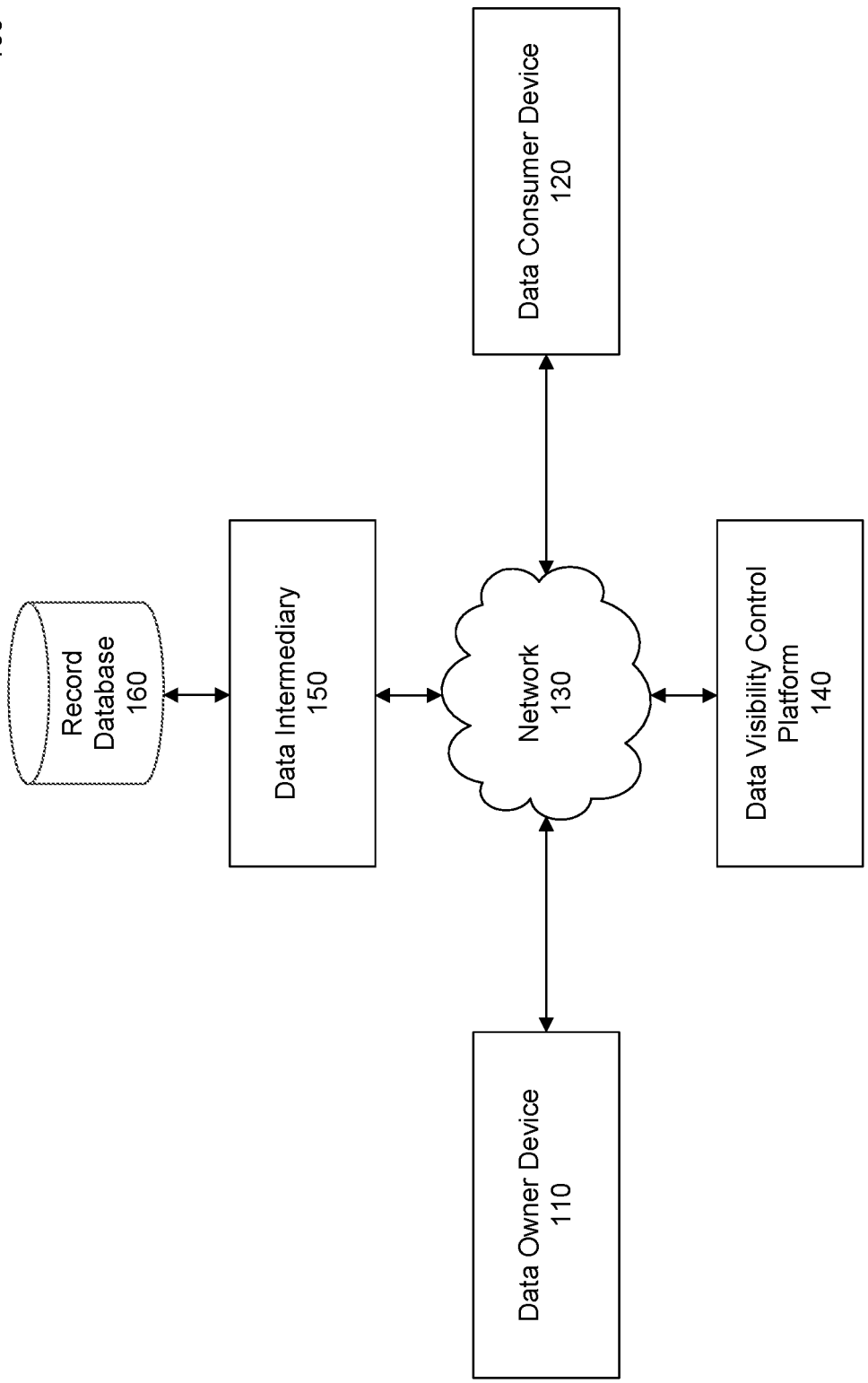
FIG. 1A-1B depicts a block diagram of a record-level encryption environment, according to some embodiments.

Provided herein are system, apparatus, device, method and/or computer-program product (non-transitory computer-readable storage medium or device) embodiments, and/or combinations and sub-combinations thereof, for a record-level encryption scheme for a data-ownership platform.

Disclosed herein are systems and methods for a record-level encryption scheme that decentralizes data visibility control, vesting such control in the data owner such that data owners and data consumers (e.g., a service provider, a data requester, etc.) may interact with each other, allowing the data owner to control granting, denying, and revoking access (among other actions) to data of a data owner. Although described and depicted in the drawings as a "data consumer," a skilled artisan would understand that the systems and methods described herein apply to any entity that generates data on behalf of or associated with the data owner (such as a healthcare provider who generates a patient health record for the data owner) and/or any entity that seeks access to data of the data owner (such as an mortgage underwriter who seeks to review financial information of the data owner to complete the underwriting process).

Consent management and data visibility may be decoupled to allow data consumers to send a request to the data owner to access their data, without the data intermediary acting as a liaison between data owners and data consumers for data visibility. Additionally, data owners are able to grant, deny, and/or revoke access to their data without the data intermediary acting as a liaison. Data intermediaries may store user data, encrypted by the data owners as described below, while also governing access to the data repositories and implementing their own security protocols. To generate the encrypted records stored by the data intermediaries, data owners and data consumers may interact to grant, deny (e.g., reject), and revoke access through services provided by the data intermediary. While data intermediaries provide communication services between data owners and data consumers, they do not have visibility over data owner's records, as they are unable to decrypt them. The disclosed systems and methods may also allow a data owner to grant, deny (e.g., reject), and revoke access for one or more data consumers on a large scale, e.g., record-level access, one or more groups of related records, all of the data owner's data managed by a certain data intermediary. This gives the control of data visibility directly to the data owner.

According to the embodiments disclosed herein, aspects of the present disclosure include one or more systems and methods for record-level encryption of data. In some embodiments, the systems and methods described herein provide a party, such as a healthcare provider, the ability to generate a new record (e.g., file(s), document(s), and/or other types of digital content not limited to text such as video, audio, and images) and encrypt the record to preserve consent management with a data owner, such as a patient. Some embodiments describe systems and methods for a party (e.g., a data consumer) who may be the same party who generated the record (such as the healthcare provider in the example above) or a different party (such as an insurance company) to request access to the previously generated record that was stored by a data intermediary in an encrypted format. A data owner may be the subject of the data in the record (such as the patient in the example above). In some embodiments, the data owner may not generate the record, but be the owner of the record and data within the record. For example, a doctor may generate a patient file. While the data owner (e.g., the patient) may not have generated the file or data within the file, the patient may be the owner of the data (e.g., the patient's personal health data). For files, such as patient files, that contain sensitive information (e.g., health data, personal identifiable information (PII), and/or other data regarded as sensitive or requiring consent to view) the data owner may not manage the storage of those files; a third party (e.g., data intermediary) may be responsible for data storage. However, before a party is able to generate, access, view, edit, delete, etc., the records/files associated with the data owner, the data owner may have to give consent. Further, the data owner may decide to provide limited consent to a party, for example to only do one or more of generating, accessing, viewing, editing, or deleting records, and may limit the access of parties to only certain records or to certain records for certain periods.

The record-level encryption scheme allows a data owner to have consent management over their data, even though a third party may be managing the storage and security of the data. For example, when a patient wants to grant access to a health care professional to generate a new record for their file or patient profile, the patient may be able to grant access to the health care professional for the specific file. The patient may also give access to read, view, edit, and delete individual records within the patient file or profile. This provides an advantage over current systems that do not give data owner's the ability to grant, deny (e.g., reject), and revoke access to their data on an individual record-level. Conventional systems use a centralized approach where a data intermediary and/or a third-party broker provides storage, security, and data access services. However, the systems and methods disclosed herein provide a decentralized approach, which may allow the data owner and a data consumer to interface via a data visibility control platform application programming interface (API), such as by exchanging messages via a communications network. For example, the data owner may grant, deny (e.g., reject), and/or revoke consent for individual data consumers to read, write, edit, delete, etc., the data owner's data via the data visibility control platform API. The data owner may grant, deny (e.g., reject), and/or revoke access to specific data (e.g., files or records) of specific data consumers.

As described above, a data owner may be the subject and/or the legal owner of the data, even if they are not the generator and/or custodian of the data. A data consumer (e.g., user or requester) may be a person or entity that generated the data or a person or entity seeking access to the data owner's record(s), file(s), account, and/or the like. For example, a data owner may be a patient and a data consumer may be a doctor, a caregiver, or other healthcare provider. The data consumer could also be an insurance company, a different health care provider who cares for the patient (such as a specialist who seeks to review a primary care physician's notes), or a family member who is preparing a family medical history, to name a few examples. As would be apparent to a skilled artisan, the disclosure is not limited to the medical or insurance industries, and is applicable in any other context in which one party owns data and another party seeks to use or request access to the data. For example, the data owner may be an employee and the data consumer a human resources professional; the data owners may be citizens and the data consumer a governing body; the data owner may be a consumer (e.g., purchaser) and the data consumer a retail or utility organization; and the data owner may be an account holder and the data consumer a financial institution. There are many possible embodiments where a data owner and data consumer may use the record-level encryption scheme to provide decentralized consent management for the records of the data owner and the examples provided herein are not intended to be limiting. The framework for decentralized consent management of records described herein is applicable where a centralized entity generates data records on behalf of a data owner, which are then stored in centralized data storage. The framework is also applicable to artificial intelligence (AI) applications that use data to train AI models. The framework would allow data owners to choose which of their data records could be used to train an AI model.

Various embodiments of the disclosed technology will now be discussed with respect to the corresponding figures.

FIG. 1A depicts a block diagram of a record-level encryption environment 100, according to some embodiments. Record-level encryption environment 100 may include one or more data owner device 110, one or more data consumer device 120, network 130, data visibility control platform 140, and one or more data intermediary(ies) 150. In some embodiments, data owner device 110 and data consumer device 120 may communicate over network 130. Network 130 may facilitate communications between data visibility control platform 140 and devices accessing network 130, such as data owner device 110 and data consumer device 120. Data owner device 110 and data consumer device 120 may access data visibility control platform 140 over network 130 via an API (e.g., web-server application, web-client application, and/or native application). Data owner device 110 and data consumer device 120 may utilize data visibility control platform 140 to generate, delete, edit, view, and/or read records containing data of the data owner.

Data owner device 110 and/or data consumer device 120 may use hardware or software capable of generating and securely storing cryptographic keys to encrypt and decrypt payloads, e.g., records, cryptographic keys, and/or other data transmitted between devices in record-level encryption scheme 100. In some embodiments, data owner device 110 and data consumer device 120 may be a smart phone, smart watch, desktop, laptop, notebook computer, netbook, tablet, personal digital assistant (PDA), and/or other communication devices which may be used to communicate over network 130, to name a few non-limiting examples. In some embodiments, an application (which may or may not be browser-based) may provide a user interface for data visibility control platform 140 on data owner device 110 and/or data consumer device 120. Selectable objects, buttons, or other interface elements may be provided for a user to register for data visibility control platform 140, grant/deny/revoke access for data consumers, encrypt/decrypt records, and generate, delete, edit, view, and/or read one or more records, to name a few non-limiting examples.

The record-level encryption scheme disclosed herein may employ symmetric, asymmetric, and/or hybrid cryptography. In some embodiments, data owner device 110 may generate cryptographic keys, such as those described in FIGS. 2A, 2B, and 2C. The cryptographic keys may include one or more public-private key pairs of the data owner, one or more public-private key pairs of the data consumer, as well as record keys that are used to encrypt records stored in record database 160. In some embodiments, a hybrid encryption model using both symmetric and asymmetric encryption schemes may be utilized.

Record-level encryption environment 100 may include network 130. Network 130 may be a wireless network and/or a combination of wired and wireless networks. For example, network 130 may include a packet-switched network (e.g., internet protocol-based network), a non-packet switched network (e.g., quadrature amplitude modulation-based network), and/or the like. According to some aspects of this disclosure, network 130 may include network adapters, switches, routers, modems, and the like connected through wireless links (e.g., radiofrequency, satellite) and/or physical links (e.g., fiber optic cable, coaxial cable, Ethernet cable, or a combination thereof). According to some aspects of this disclosure, network 130 may include public networks, private networks, wide area networks (e.g., Internet), local area networks, and/or the like. According to some aspects of this disclosure, network 130 may provide and/or support communication from a telephone, cellular phone, modem, and/or other electronic devices. For example, network 130 may include and support communications among data owner device 110, data consumer device 120, data visibility control platform 140, and/or data intermediary 150 via network 130.

Record-level encryption environment 100 may include data visibility control platform 140, which may manage secure access to stored data. Data visibility control platform 140 may provide a platform for data owners and requesters to register for a record-level encryption scheme. In some embodiments, data visibility control platform 140 may also track whether access to records have been granted, denied, or revoked from a data owner to a requester. Data visibility control platform 140 may also provide an infrastructure and method for data owners to interface with data consumers. In some embodiments, data owners and data consumers may first register within data visibility control platform 140. When a data owner registers with data visibility control platform 140, the data owner may provide sufficient information to authenticate themselves and allow data visibility control platform 140 and data intermediary 150 to identify existing data of the data owner, e.g., records, files, and/or other forms of electronically stored data associated with the data owner. For example, the data owner may be required to submit an identifier capable of verifying their identity such as a social security number, Public Digital Identity System (SPID) credentials, or other credentials. In some embodiments, data visibility control platform 140 may require multiple identifiers such as both a: (1) social security number; and (2) copy of a birth certificate.

In some embodiments, data consumers may register with data visibility control platform 140 as entities and/or individuals. For example, in the health care system, a patient may register with data visibility control platform 140 and the full patient file may then be associated with the data owner, e.g., patient, such that the patient may begin to grant, deny, and revoke access to a data consumer. A data consumer, e.g., a health care professional, may register to request access to existing patient files, edit and review patient files, and/or generate additional patient files to be electronically stored and managed by data intermediary 150. Similar to the data owner, data consumers may also be required to submit one or more identifiers to verify their identity.

Data visibility control platform 140 may be accessed by a web browser, a hybrid or a native web application, and/or application programming interface (API), etc., which is accessible by data owner device 110 and/or data consumer device 120. Data visibility control platform 140 may utilize backend services to process and store data owner and data consumer registration. Data visibility control platform 140 may also process and store data consumers' granted, denied, or revoked access status for data owner records. In some embodiments, data visibility control platform 140 may be utilized for backend services to provide direct communication between data owners and data consumers. Under a conventional approach, data owners have little control over their data-rather, the party who creates the data (e.g., a medical provider generating a medical record of a patient's visit) typically controls access to the data, often via a third-party data intermediary (e.g., a medical records service). For example, a medical provider may generate a record of a patient's visit, and provide the patient with access to the record via a patient portal (which may be maintained by a third-party service provider). Typically, the patient does not control their own data; that is, they cannot grant, deny, or revoke access rights to their medical records. By contrast, the data visibility control platform 140 empowers data owners to control their data. Data owners and data consumers may communicate with each other, without interfacing indirectly through a data intermediary, to grant/deny/revoke access to records of a data owner. In some embodiments, data intermediary 150 may confirm a data consumer has access to record(s) of a data owner via data visibility control platform 140. This provides a significant advantage over conventional systems, particularly when a data owner's records may be stored by multiple data intermediaries and a data owner may have to interface with each data intermediary to control visibility of their data (e.g., records). Data visibility control platform 140 provides an interface to control data visibility in real-time, regardless of the data intermediary storing the data owner's data.

Figure 1B:
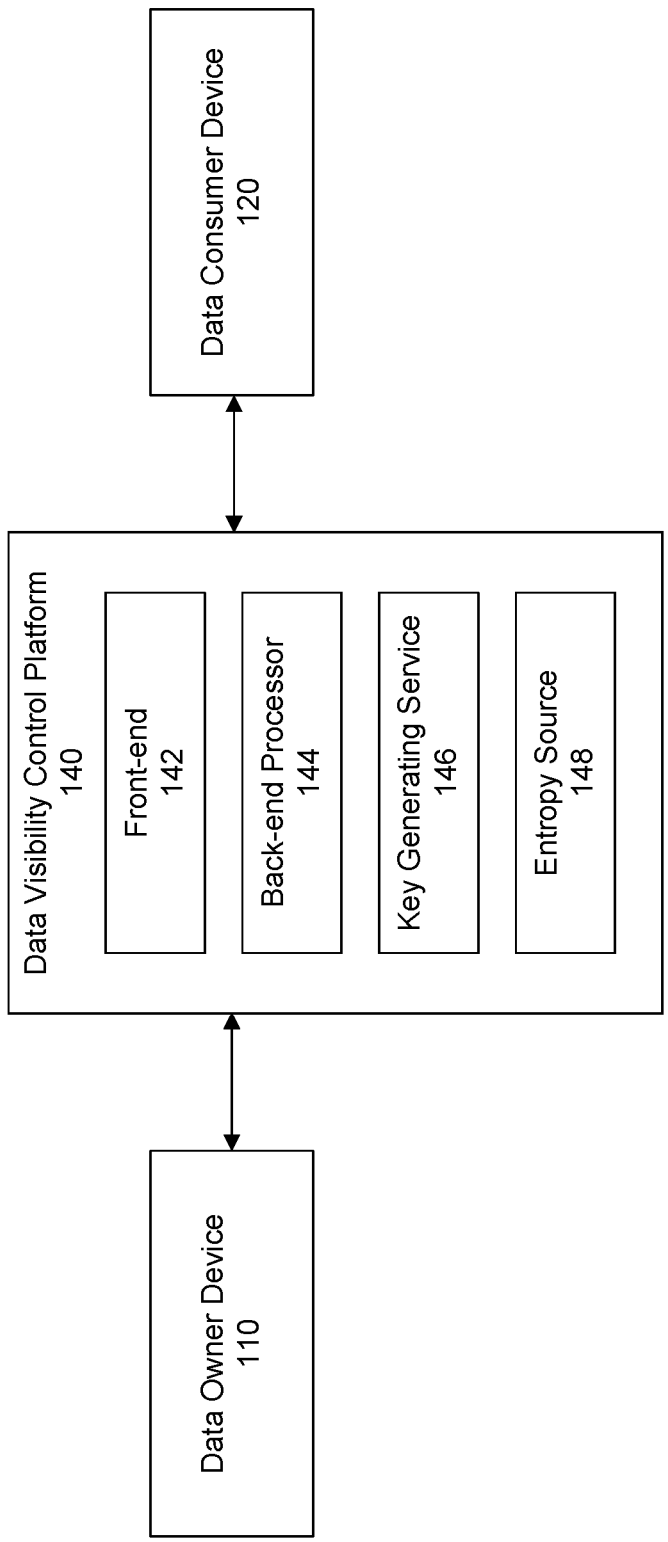

In some embodiments, data visibility control platform 140, as described in FIG. 1B, may provide infrastructure or access to third party services including front-end 142, back-end processor 144, key generating service 146, and/or entropy source 148 to be used by data owner device 110 and/or data consumer device 120. The back-end processor 144, key generating service 146, and/or entropy source 148 may be used to generate the various public and private cryptographic keys for data owner device 110 and/or data consumer device 120 that are used in the asymmetric, symmetric, and/or hybrid encryption schemes disclosed herein. In some embodiments, data owner device 110 and/or data consumer device 120 may interact with front-end 142 and data visibility control platform 140 using back-end processor 144 and/or key generating service 146 for encryption and decryption of records. Additionally, back-end processor 144 may be used to add additional security measures, such a digital signatures and/or digital certificates.

In some embodiments, record-level encryption environment 100 may include data intermediary 150 and record database 160. Data intermediary 150 may provide security and storage services for the data of the data owner. In some embodiments, the data may be in the form of records, files, and/or other forms of electronically stored data associated with the data owner. In some embodiments, data may be generated, read, and/or edited via a data owner device 110 and/or data consumer device 120. Record database 160 may be managed by data intermediary 150. In some embodiments, data owners and consumers may not interact with data intermediary 150 and/or record database 160. Data owners and consumers may interact with each other and with data visibility control platform 140. Data visibility control platform 140 may communicate any grant or revocation of access to data by the data owner with data intermediary 150, which may be responsible for access governance and security protocols of the stored data. In some embodiments, data visibility control platform 140 may store the access status for data owner records and data consumers and provide the status to data intermediary 150 upon request from data intermediary 150. In some embodiments, data visibility control platform 140 may provide the status to data intermediary in real-time, in response to a change in status, and/or periodically. Additionally, for data and/or record access, data visibility control platform 140 may provide the platforms to electronically share the record. In some embodiments, data visibility control platform 140 and/or data intermediary 150 may utilize a data sharing platform to provide access to the data and/or records stored via record database 160. The data intermediary platform may also be responsible for security and/or privacy control functions. For example, data sharing based on message queuing protocols, such as AMQP, etc., may be utilized by data visibility control platform 140 and/or data intermediary 150. Regardless of the protocol used for data sharing, the data visibility control platform 140 may provide secure data and provide secure access to the data using hardware- and/or software-based security techniques.

As described above, record database 160 may store encrypted records generated by data owners and/or data consumers. Data and/or records stored in record database 160 may be accessed by the data owner and/or data consumers that have been granted records access through data visibility control platform 140. Record database 160 may store data and/or records on-site, remotely, or a combination of both. In some embodiments, data intermediary 150 may employ a plurality of records databases 160. Additionally, in some embodiments, record database 160 may be a third-party database, data broker, one or more blockchains, and/or a data storage service.

FIG. 1B depicts a detailed block diagram of an example data visibility control platform 140 and interactions with data owner device 110 and data consumer device 120 in record-level encryption environment, according to some embodiments. Communications may occur through a communication network, such as network 130 of FIG. 1A. Data visibility control platform 140 may include or provide data owner device 110 and/or data consumer device 120 access to front-end 142, back-end processor 144, key generating service 146, and/or entropy source 148. Data visibility control platform 140 may use front-end 142, back-end processor 144, key generating service 146, and/or entropy source 148 to register data owner device 110 and/or data consumer device 120, generate cryptographic keys (such as the public and private keys described herein), and/or allow data owners to grant/deny/revoke access to the data owner's data (e.g., data owner's records containing sensitive information).

This intermediate stack of components 142-148, including front-end 142, back-end processor 144, key generating service 146, and entropy source 148 may optionally be centralized, distributed, or otherwise decentralized. Any key generating service 146 and entropy source 148 are optional with respect to data visibility control platform 140. For example, data owner device 110 and data consumer device 120 may be configured to generate their own cryptographic keys (e.g., public-private key pairs, record keys, private (shared) keys).

In some embodiments, front-end 142 may provide a user interface for the data owner and/or data consumer. The user interface may be accessed via a web browser, hybrid or native web application, and/or application programming interface (API), etc., accessible on data owner device 110 and data consumer device 120. This interface may allow the data owner to maintain visibility over data consumers. For example, front-end 142 may display the data consumers who have been granted access to records or data of the data owner or had access revoked. Front-end 142 may further display requests by data consumers that have been denied. The data owner may be able to grant, deny, or revoke access by interacting with the user interface displayed by front-end 142 on data owner device 110. Front-end 142 may also be used by the data owner to grant, deny, and revoke data access to any given data consumer, at any time, for any reason. For example, front-end 142 may display a request from a data requester such as data consumer device 120. The request may include various information such as an identity of the data requester, a time, a reason, and/or a location from which the request originated. The data owner may use front-end 142 to grant or deny the request. In some embodiments, these operations may be executed by back-end processor 144.

Figure 2A:
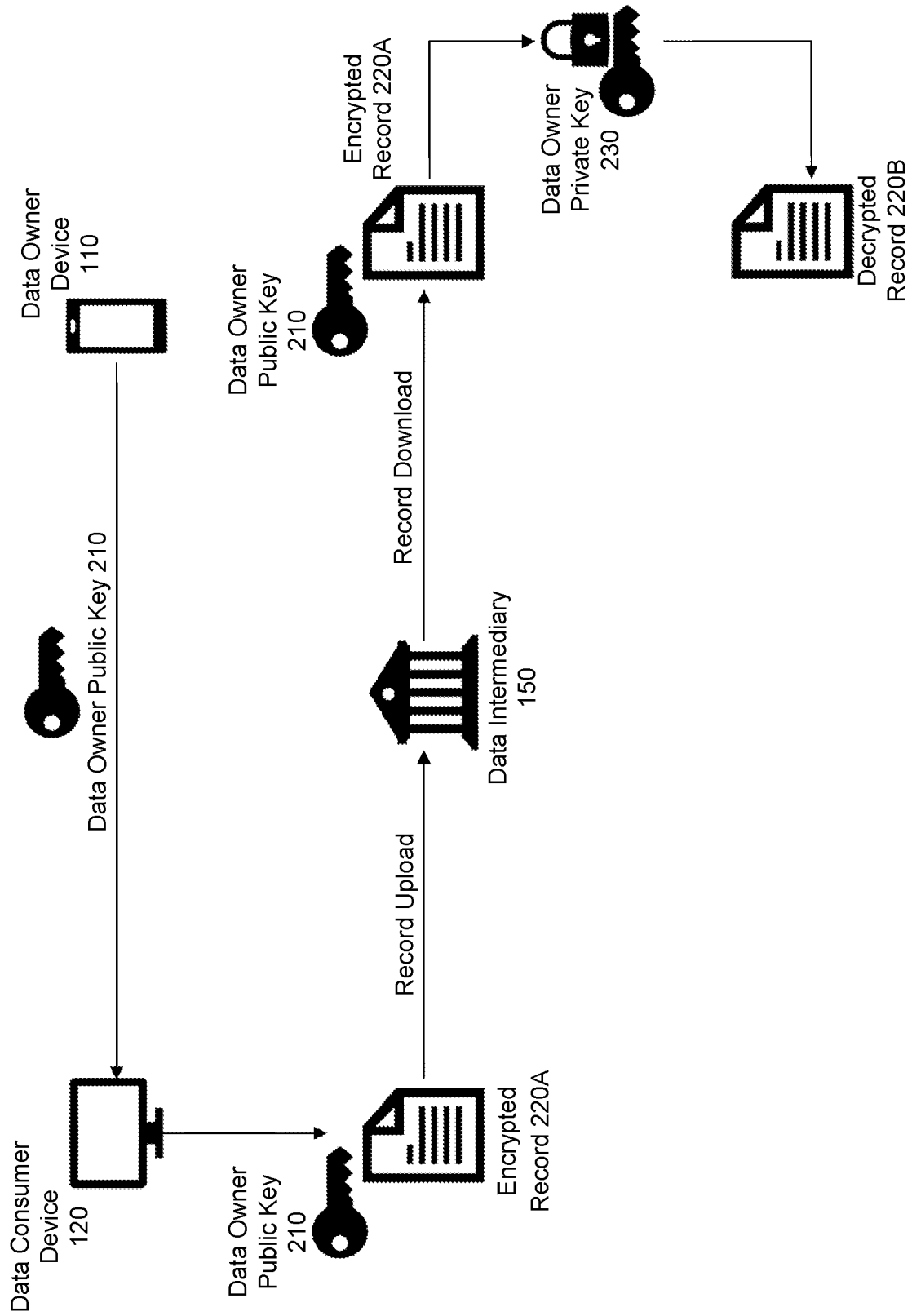
FIGS. 2A-2B depict example processes for providing record-level encryption for a newly generated record, according to some embodiments.
Figure 2B:
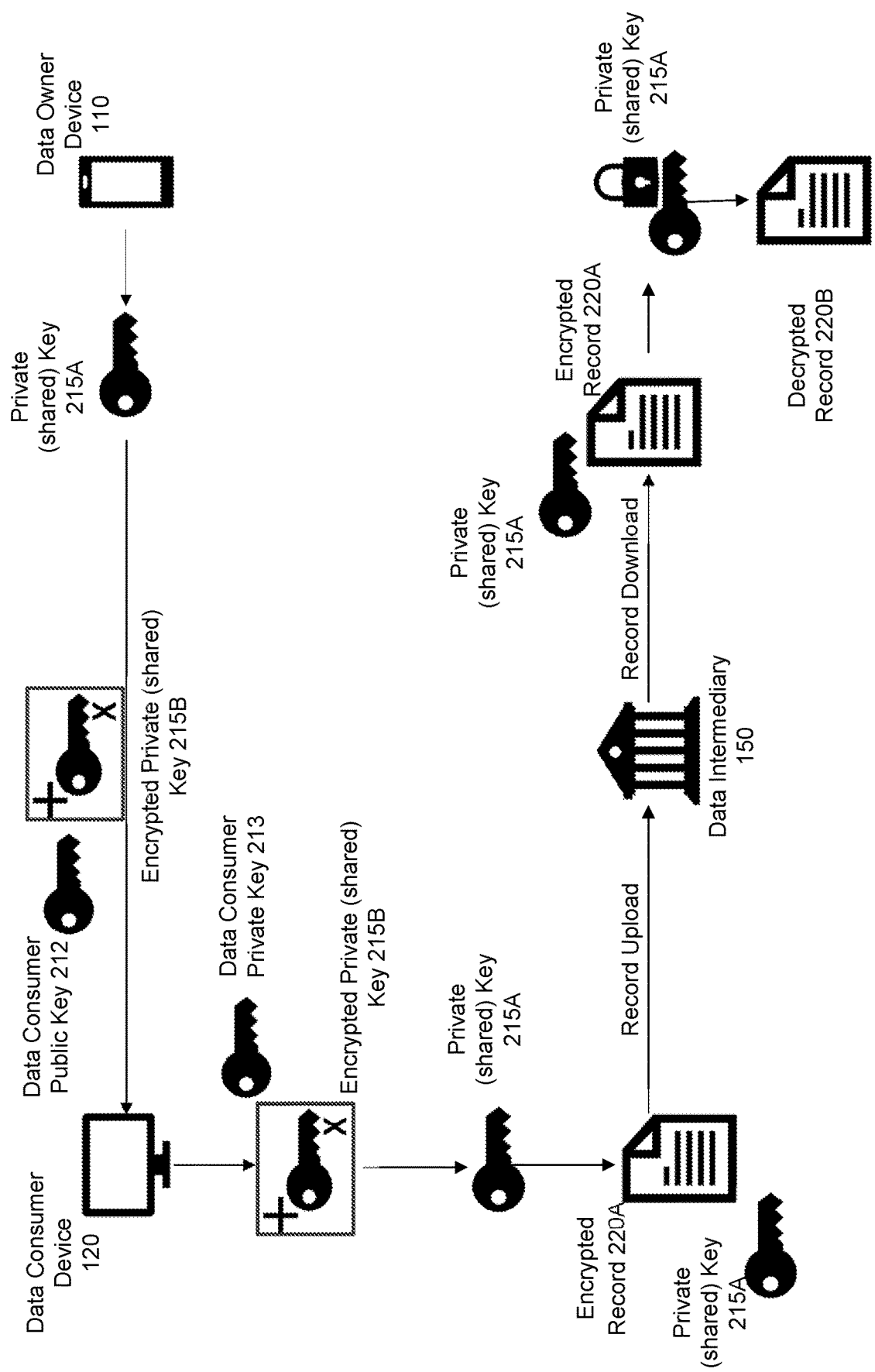
Figure 2C:
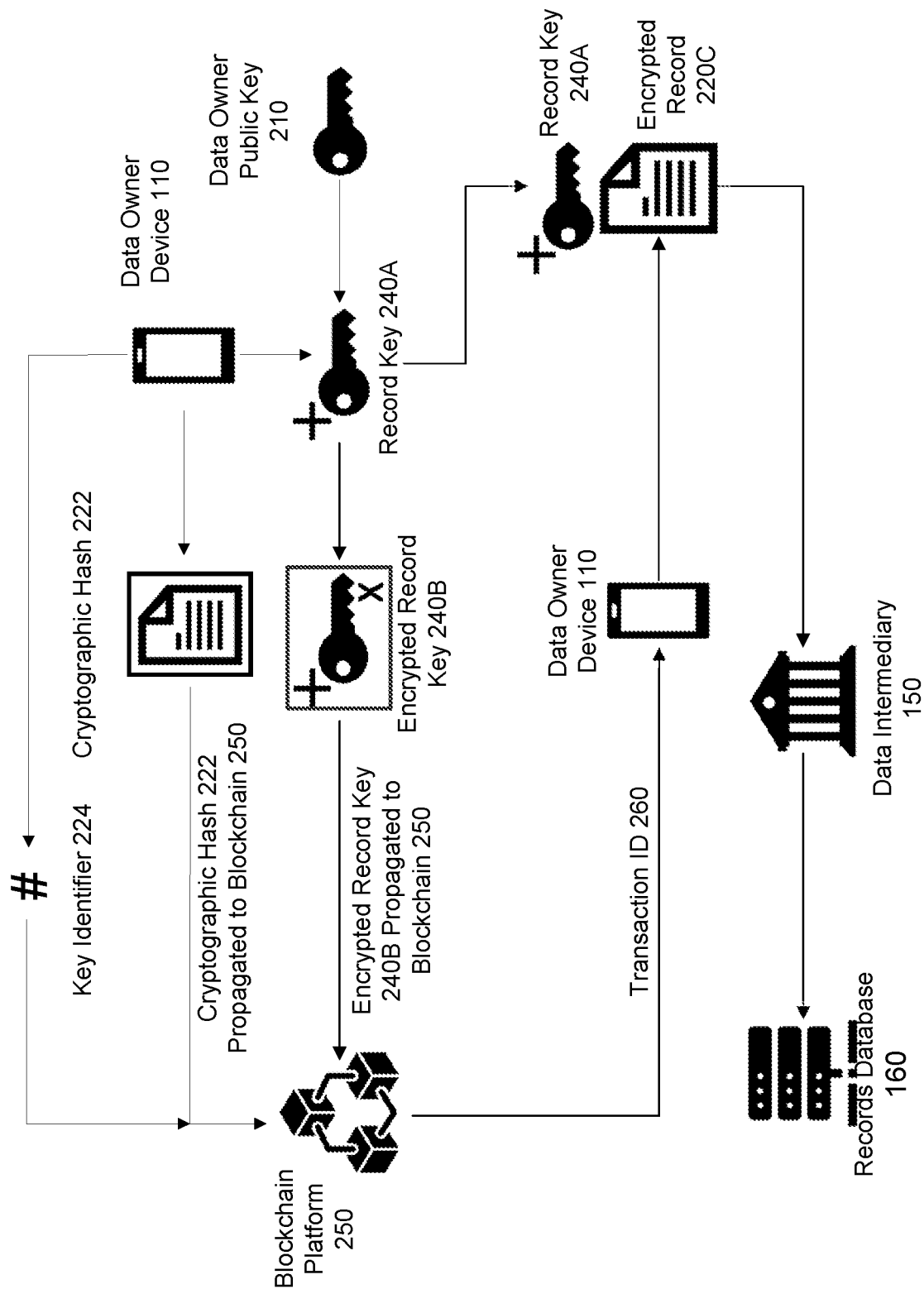
FIG. 2C depicts an example process for storing an encrypted record in a records database using a record-level encryption scheme.
Figure 4A:
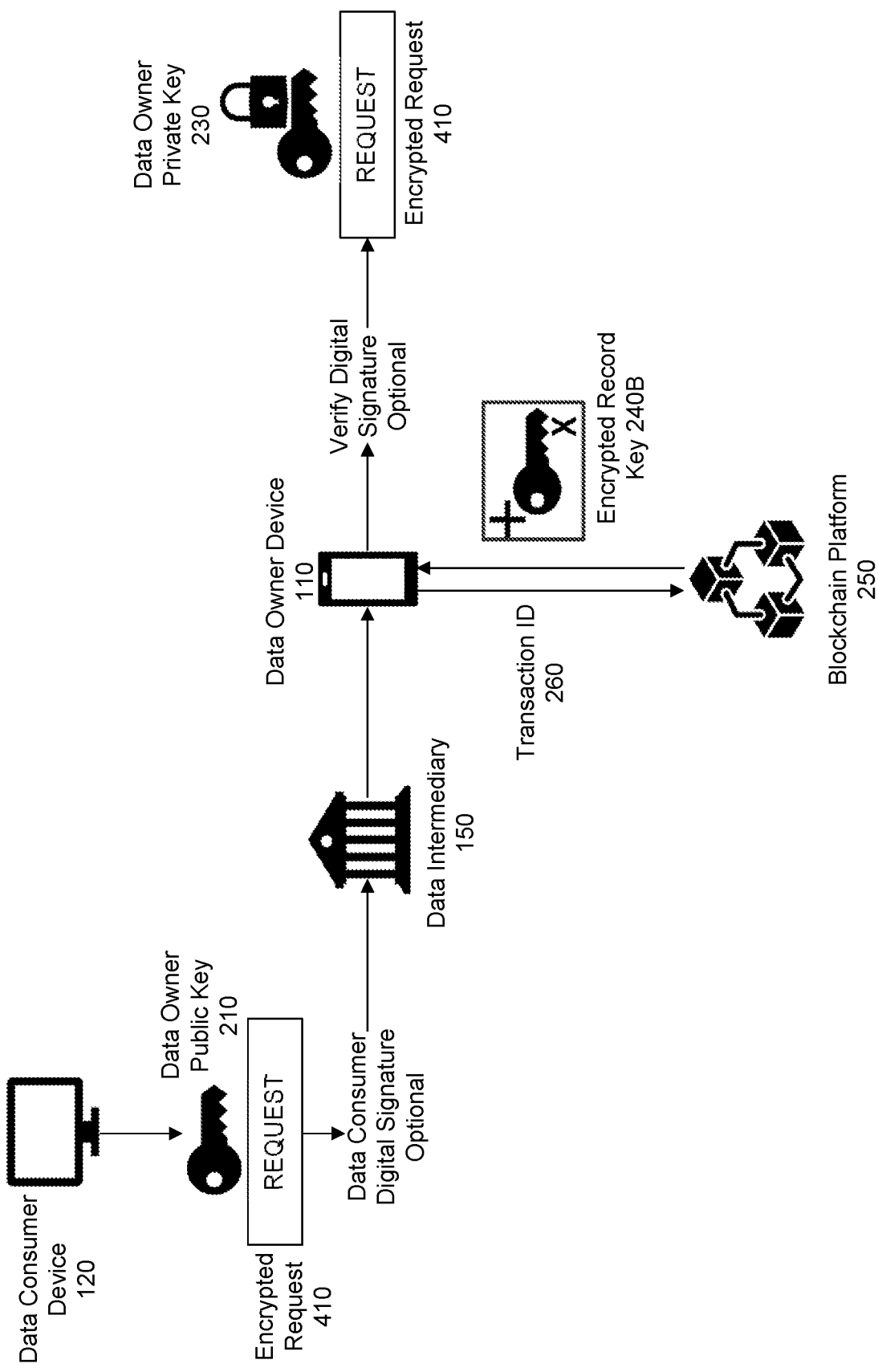
FIGS. 4A-4C depict an example process for providing requester access to read a record stored with record-level encryption, according to some embodiments.
Figure 4B:
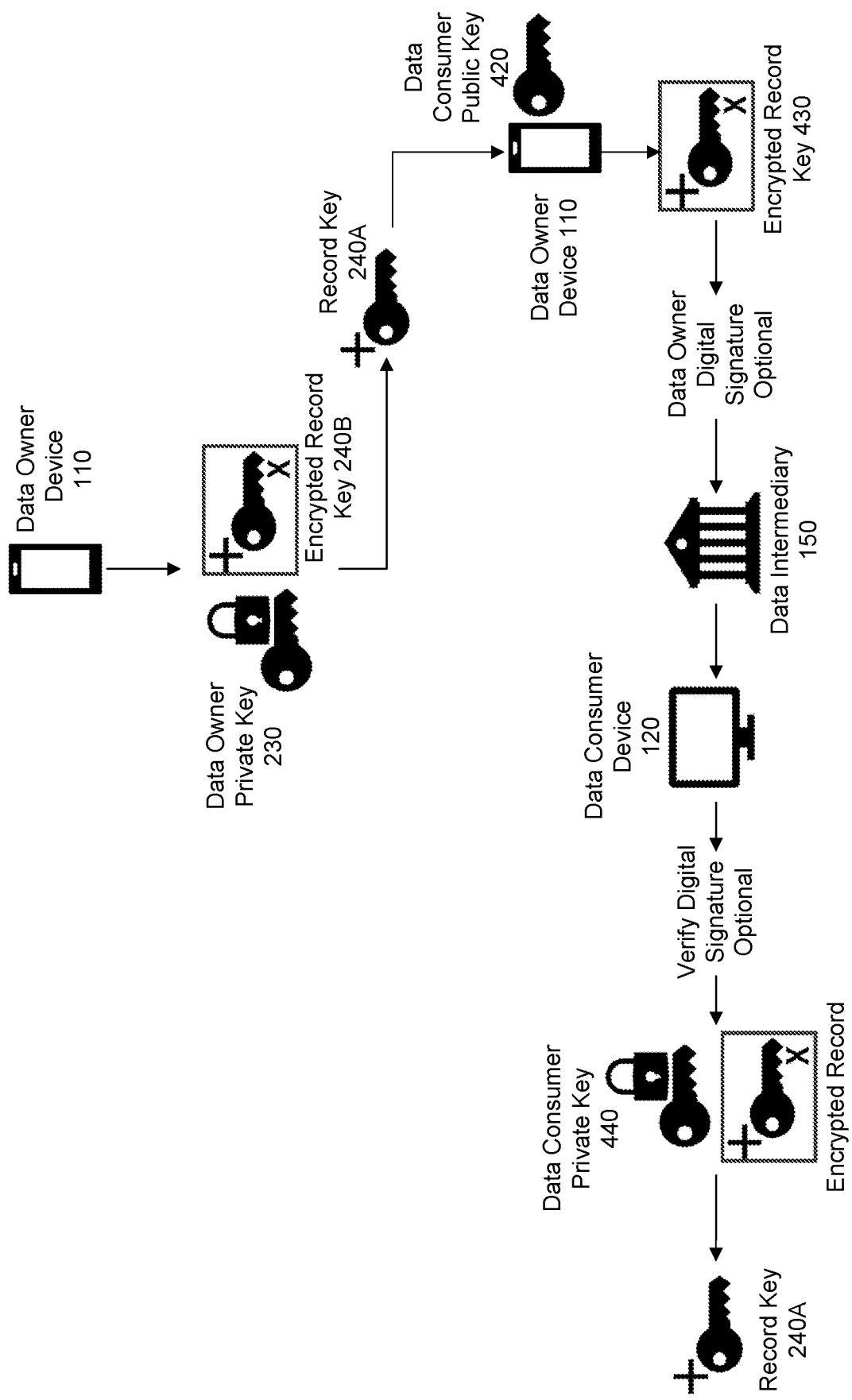
Figure 4C:
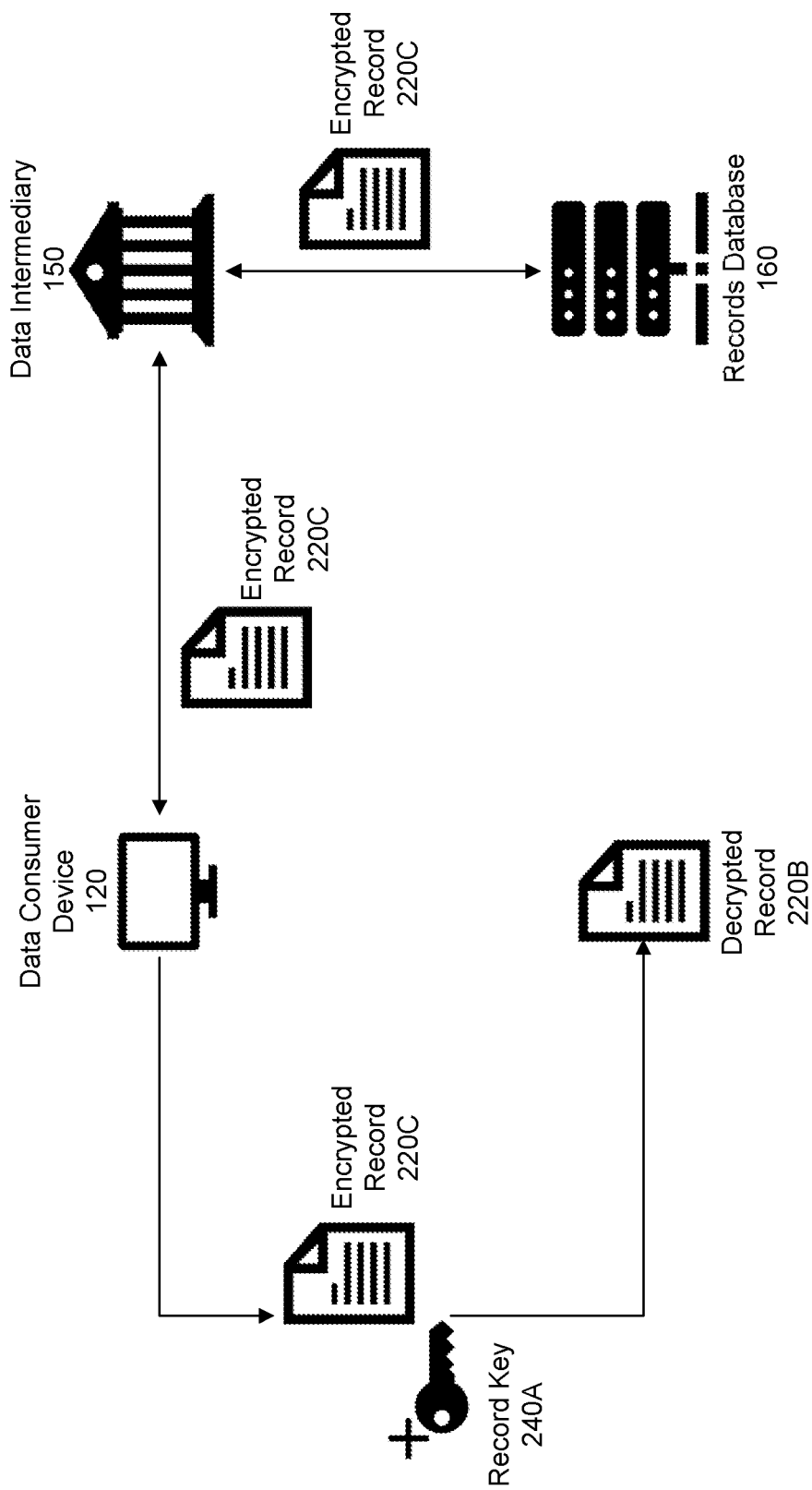

As described in FIGS. 2A-2C, a data consumer may seek to generate a record containing sensitive or confidential data of a data owner, additionally a method for reading records is described in FIGS. 4A-4C. These described methods use cryptographic keys to securely transmit the sensitive data of the data owner. The components of FIG. 1B may be used by data owner device 110 and/or data consumer device 120 to generate cryptographic keys. Data visibility control platform 140 may provide access to and/or use front-end 142, back-end processor 144, key generating service 146, and/or entropy source 148 to generate cryptographic keys to encrypt and decrypt the data (e.g., records) and/or other cryptographic keys. For example, back-end processor 144 or key generating service 146 may have at least one entropy source by which to provide random seed data for cryptographic key generation, either at the back-end processor 144, data owner device 110, and/or at data consumer device 120, according to some embodiments.

In some embodiments, data owner device 110 and/or data consumer device 120 may generate cryptographic keys to transmit data and/or cryptographic keys within record-level encryption environment 100 as described with reference to FIGS. 2A-2C and 4A-4C. For example, data owner device 110 may generate the public and private keys that are used to encrypt and decrypt records and/or other cryptographic keys. Data owner device 110 may also generate one or more record keys. Data owner device 110 and data consumer device 120 may include hardware and/or software capable of generating and securely storing cryptographic keys. In some embodiments, data owner device 110 and/or data consumer device 120 may generate public and private keys (including public-private key pairs) when the data owner and/or the data consumer register for data control visibility platform 140. In addition or as an alternative to storing keys locally on the data owner device 110 or data consumer device 120, certain keys may be sent to a key vault and stored for later use to execute the methods described in FIGS. 2A-2C and 4A-4C. As described in more detail below, asymmetric cryptography, symmetric cryptography, and/or a combination of both (hybrid encryption) may be used to exchange information within the system disclosed herein.

In some embodiments, multiple sets of public-private key pairs may be utilized. For example, a first public-private key pair may be used for communication between data owner device 110 and data consumer device 120 (e.g., a communication key pair). A second public-private key pair may be generated for encrypting and decrypting record keys (e.g., a key encryption pair). Utilizing two sets of key pairs may be beneficial to increase network and computer security within record-level encryption environment 100. Each key pair may be updated or changed at different frequencies based on various needs. As will be discussed below with reference to FIGS. 3A, a key identifier or key index may be stored in association with the public-private key pairs to determine which public-private key pair was used to encrypt a record, a record key, and/or a communication.

For example, a first record may be encrypted using public-private key pair A. Next, a new public-private key pair B may be generated and used to encrypt subsequent records. When a request to decrypt the first record is received, a lookup may be performed to identify that key pair A was used to encrypt the first record. As a result, key pair A, instead of key-pair B, may be used to decrypt the first record.

Additionally, keys used to encrypt and decrypt records may be updated or rotated. As will be discussed in more detail below, record keys may be used to encrypt records stored in record database 160. The record key may be encrypted using a data owner's private key, and then stored. In some embodiments, the encrypted record key may be stored in a storage device. In some embodiments, the storage device includes a blockchain platform. The data owner may update the record key. The record key may be updated at any frequency such as once an hour, once a day, once a week, once a month, once a quarter, to name a few non-limiting examples. Events other than the passage of time may also trigger updating one or more record keys, such as suspicious activity associated with the data owner, which may include suspicious activity targeting the data owner or suspicious activity from a data owner themselves, such as activity that is inconsistent with the data owner's past behaviour (such as suddenly granting record access to a large number of data consumers) or granting access to a known fraudulent entity. When the record key is updated, the data owner may choose to re-encrypt the records that were encrypted using the previous record key. Here, the data owner may perform a re-encryption process using the new record key.

To perform this operation, the data owner may retrieve the encrypted record from storage (e.g., record database 160) and retrieve the encrypted record key from the blockchain platform. The data owner may then decrypt the encrypted record key using a private key. The data owner may then decrypt the encrypted record with the record key. Subsequently, the data owner may generate a new record key, and use it to encrypt the record. Once encrypted, the record may be stored at record database 160. The new record key may also be encrypted using a private key, and stored on a blockchain platform. In some embodiments, the data owner may delete the old record key. As discussed above, a key identifier may be stored in association with the encrypted record key. The key identifier may correspond to the private key used to encrypt and decrypt the encrypted record key. In some embodiments, a transaction identifier may be generated and used to map an association between: (1) an encrypted version of a record; (2) a cryptographic hash of an unencrypted version of the record; (3) a key used to encrypt the record (e.g., an encrypted record key); and (4) a key identifier corresponding to a key used to encrypt the record key. The data owner may generate and use a new record key every time the data owner encrypts a record.

In some embodiments, certain private keys may be shared with trusted parties. For example, data owner device 110 may be configured to share certain private keys with law enforcement in the event of a criminal investigation. Similarly, data owner device 110 may be configured to share certain private keys with medical personnel, a designated family member, a medical proxy, etc., during a medical emergency.

FIG. 2A depicts an example process for providing record-level encryption for a newly generated record that employs asymmetric cryptography. For the purposes of the example provided in FIG. 2A, the data owner and the data consumer have previously registered with data visibility control platform 140.

In the embodiment of FIG. 2A, data owner device 110 employs asymmetric cryptography (or public-key cryptography) to generate and/or store at least one public-private key pair (e.g., data owner public key 210 and corresponding data owner private key 230). The public-private key pair may have a corresponding identifier. The identifier may be any value used to uniquely identify the key pair (e.g., a letter, number, word, and phrase). In some embodiments, the public key may be used as the identifier. In some embodiments, data owner device 110 may also generate and/or store one or more individual encryption keys, such as private, record keys that are discussed in more detail below. Identifiers may also be generated for individual encryption keys. In some embodiments, a third-party certificate authority may generate a public-private key pair for data owner device 110. Keys may be stored locally at data owner device 110, at third-party storage, or a combination thereof. For example, private keys may be stored in computer memory that is secured using hardware and/or software techniques to prohibit unauthorized access to the private keys. In some embodiments, data owner device 110 may store generated encryption keys in a third-party key vault, such as a remote secure vault. In some embodiments, data owner device 110 may store encryption keys in a cold storage system without internet access. In some embodiments, key identifiers may be stored at the same location as the keys they identify.

In some embodiments, data owner device 110 transmits one or more data owner's public keys, such as data owner public key 210, to data consumer device 120 via network 130 communication. Data owner device 110 may also publish or post (e.g., to a website) or broadcast the one or more data owner public keys, such as data owner public key 210, such that data consumers can access the one or more data owner public keys. Data owner device 110 may publicize the one or more data owner public keys, wherein publicizing includes transmitting, broadcasting, publishing, posting, and/or any other mechanism for publicly disclosing data owner public keys. To further enhance security, keys generated by the data owner or the data consumer may expire after a certain period (e.g., 1 hour, 1 day, 1 week, 1 month, etc.) or based on a triggering event (e.g., a record was accessed 5 times, a record was edited, a record was sought to be accessed with a high frequency (which may indicate fraudulent attempts, etc.), and new keys may be generated and used. New keys may be generated and used a regular time intervals, on demand, or based on triggering events.

The data owner may utilize an interface of data visibility control platform 140 to transmit one or more data owner public keys, such as data owner public key 210, to a specified data consumer device 120. In some embodiments, prior to sending data owner public key 210, data owner may receive a notification that the specified data consumer requests the ability to generate one or more documents that will be associated with the data owner and stored via data intermediary 150 and/or record database 160. In some embodiments, when a data owner grants access to an entity to generate and/or delete records associated with or on behalf of the data owner (such as a healthcare provider), the entity may be granted the ability to repeat the process described herein to generate new records containing data of the data owner as needed until access has been revoked. For example, a patient (data owner) may grant their primary care physician the ability to generate multiple records, each of which is encrypted and stored using the systems and methods described herein.

Data consumer device 120 may receive data owner public key 210 from data owner device 110. Data consumer device 120 may generate a record, e.g., file, document, and/or electronically stored data, including data of the data owner. In some embodiments, the data may be sensitive and or confidential data of the data owner, such as medical information, health data, financial data, PII, and/or similarly sensitive and/or confidential data. Data consumer device 120 may use data owner public key 210 to encrypt the newly generated record. Data consumer device 120 may include hardware and/or software capable of generating cryptographic keys and encrypting records. Data consumer device 120 may access one or more web applications and/or native applications, e.g., for general-purpose computers (PC, kiosk, etc.), mobile devices (e.g., tablet, smartphone, etc.), to encrypt the record (e.g., encrypted record 220A). Data consumer device 120 may provide a user interface for data visibility control platform 140.

In some embodiments, encrypted record 220A, encrypted with data owner public key 210, may be uploaded from data consumer device 120 to data intermediary 150 via network 130. Data consumer device 120 may interact with the user interface of data visibility control platform 140 via front-end 142, to upload encrypted record 220A to data intermediary 150.

Data intermediary 150 may receive encrypted record 220A. Data intermediary 150 may transmit a notification to data owner device 110 comprising a message indicating encrypted record 220A has been uploaded from data consumer device 120. Data intermediary 150 may transmit the notification to data owner device 110 via network 130. In some embodiments, data intermediary 150 may transmit the notification via data visibility control platform 140. Data visibility control platform 140 may use front-end 142 to display the notification on the user interface. Data owner device 110 may receive the notification that a new record associated with the data owner and/or the data owner device 110 has been uploaded to the data intermediary 150. Similarly, in some embodiments, data consumer device 120 may transmit the notification to the data owner device 110, which may be displayed via the user interface of front-end 142.

The notification may indicate that encrypted record 220A has been uploaded from data consumer device 120. The data owner may interact with the user interface of front-end 142 to download encrypted record 220A from data intermediary 150. In some embodiments, encrypted record 220A may be downloaded from data intermediary 150 to data owner device 110 via network 130. Data owner device 110 may use data owner private key 230 to decrypt the encrypted record 220A, generating decrypted record 220B, which may be stored locally by data owner device 110. Data owner device 110 may use back-end processor 144 and/or key generating service 146 provided by data visibility control platform 140 to decrypt encrypted record 220A using data owner private key 230 to generate decrypted record 220B. Decrypted record 220B may be unencrypted, cleartext of the document that was generated by data consumer device 120. In some embodiments, decrypted record 220B may be referred to as a "clear record" or "cleartext" or "plaintext." As discussed above, the technology disclosed herein applies to any type of digital content including (but not limited to) text, video, audio, and images.

FIG. 2B depicts an example process for providing record-level encryption for a newly generated record the employs a hybrid encryption model that uses both symmetric and asymmetric cryptography. The data owner device 110 may generate a private (shared) key 215A, a copy of which is shared with data consumer device 120 with the understanding that the data owner and the data consumer do not share the private key 215A with other entities; that is, the private (shared) key 215A is a shared secret. Private (shared) key 215A may be a symmetric key used to encrypt and decrypt data. As described herein, the data owner device 110 may include the hardware and/or software necessary for generating the private (shared) key 215A or the data owner device 110 may invoke another entity, such as a third-party certificate authority to generate the private (shared) key 215A. The private (shared) key 215A, may be stored in computer memory that is secured using hardware and/or software techniques to prohibit unauthorized access to the private keys. In some embodiments, data owner device 110 may store generated encryption keys in a third-party key vault, such as a remote secure vault. In some embodiments, data owner device 110 may store encryption keys in a cold storage system without internet access.

In order to initially share private (shared) key 215A, data owner device 110 may utilize asymmetric encryption. For example, data owner device 110 may utilize data consumer public key 212 to encrypt private (shared) key 215A. The result may be encrypted private (shared) key 215B. Data owner device 110 may retrieve data consumer public key 212 via communication over network 130. Data consumer device 120 may also publish or post (e.g., to a website) or broadcast data consumer public key 212 such that data owners can access data consumer public key 212. Data consumer device 120 may publicize data consumer public key 212, wherein publicizing includes transmitting, broadcasting, publishing, posting, and/or any other mechanism for publicly disclosing data consumer public key 212. Data consumer device 120 may securely store the private (shared) key 215A using any of the same techniques described above with respect to the data consumer device 110.

Data consumer device 120 may receive encrypted private (shared) key 215B, and utilize data consumer private key 213 to decrypt encrypted private (shared) key 215B. Once decrypted, data consumer device 120 may be able to utilize private (shared) key 215A to securely exchange information with data owner device 110. For example, as discussed above, data consumer device 120 may generate a record. Data consumer device 120 may encrypt the record with private (shared) key 215A, resulting in encrypted record 220A. As stated above, data consumer device 120 may interact with the user interface of data visibility control platform 140 via front-end 142, to upload encrypted record 220A to data intermediary 150.

Data intermediary 150 may transmit a notification to data owner device 110 comprising a message indicating encrypted record 220A has been uploaded from data consumer device 120. The data owner may interact with the user interface of front-end 142 to download encrypted record 220A from data intermediary 150. In some embodiments, encrypted record 220A may be downloaded from data intermediary 150 to data owner device 110 via network 130. Data owner device 110 may use private (shared) key 215A to decrypt encrypted record 220A. As a result, data owner device 110 may view the unencrypted contents of the record (e.g., decrypted record 220B).

Using the hybrid encryption model described above, data owner may generate a private (shared) key for each data consumer with which the data owner interacts. For example, the data owner may generate private (shared) key K1 that is shared with and used to securely exchange information with their healthcare provider. The same data owner may generate private (shared) key K2 that is shared with and used to securely exchange information with their automobile insurance company. The same data owner may generate yet another private (shared) key K3 that is shared with and used to securely exchange information with their bank.

FIG. 2C depicts an example process for storing an encrypted record in a records database using a record-level encryption scheme. Data owner device 110 may generate and/or store one or more private, record keys, such as record key 240A. As discussed above, data owner device 110 may store generated keys, such as record key 240A locally or at a third-party key vault, such as within a cold storage device or remote secure vault. In some embodiments, data owner device 110 may use back-end processor 144, key generating service 146, and/or entropy source 148 provided by data visibility control platform 140 to generate record key 240A. Record key 240A may be specific to the record generated by data consumer device 120. Data owner device 110 may generate a record key 240A for each record added to data intermediary 150 and/or stored by record database 160 that is associated with the respective data owner.

Data owner device 110 may encrypt record key 240A using data owner public key 210 to generate encrypted record key 240B. Data owner device 110 may use data visibility control platform 140 to store encrypted record key 240B on blockchain platform 250. In some embodiments, data owner device 110 may further use data visibility platform 140 to store an identifier (e.g., key identifier 224) corresponding to public key 210 used to generate encrypted record key 240B. This may be beneficial in a scenario where data owner device 110 generates and uses multiple public-private key pairs, and needs to keep track of which key pair was used to encrypt record key 240A. Key generating service 146 may forward or store encrypted record key 240B to blockchain platform 250. In some embodiments, key generating service 146 may further forward or store key identifier 224 to blockchain platform 250 . . . . Key generating service 146 and/or blockchain platform 250 may use a smart-contract interface, to store encrypted record key 240B. Data visibility control platform 140 may utilize any suitable blockchain platform, such as Ethereum or another platform, e.g., supporting smart contracts, and decentralized applications, for example, but any other blockchain platform supporting similar features may be used (e.g., Hyperledger), or a non-blockchain solution (e.g., database) may be used, in some embodiments.

Data owner device 110 may be further configured to generate cryptographic hash 222 of the unencrypted record. Data owner device 110 may directly generate cryptographic hash 222. In some embodiments, data owner device 110 may use back-end processor 144, key generating service 146, and/or entropy source 148 provided by data visibility control platform 140 to generate cryptographic hash 222. Cryptographic hash 222 may be generated using any hashing algorithm, such as MD5, SHA-1, etc. Cryptographic hash 222 may be unique to the contents of the encrypted record. Data owner device 110 may transmit cryptographic hash 222 for storage at blockchain platform 250. Data owner device 110 may use data visibility control platform 140 to store cryptographic hash 222 on blockchain platform 250. Key generating service 146 may forward or store cryptographic hash 222 to blockchain platform 250.

Blockchain platform 250 may generate transaction identification (ID) 260 when data visibility control platform 140 propagates encrypted record key 240B from data owner device 110. Encrypted record key 240B may be stored on the blockchain of blockchain platform 250. In some embodiments, the blockchain may store transaction ID 260, encrypted record key 240B, and a cryptographic hash 222 of the record. Blockchain 250 may further store key identifier 224, identifying the key or key-pair used by data owner device 110 to encrypt encrypted record key 240B. FIG. 3A depicts an example of a record stored on the blockchain. Cryptographic hash 222 may be used to verify if record key 240A can decrypt encrypted record 220C. Additionally, cryptographic hash 222 can be used by data owner device 110 and/or data consumer device 120 to verify encrypted record 220C has not been tampered with. For example, data owner device 110 may retrieve (from a data intermediary) encrypted record 220C, decrypt it, and calculate the hash of the decrypted record. Data owner device 110 may then compare this hash to cryptographic hash 222 stored on blockchain 250. If the values differ, this may be an indication that the contents of the record retrieved from the data intermediary has changed or been tampered with. In some embodiments, blockchain platform 250 may store a plurality of encrypted record keys 240B and corresponding transaction IDs 260, one for each record generated by data consumer device 120. Each record may have a unique record key and transaction ID associated with storing the encrypted record key on blockchain platform 250. In some embodiments, blockchain platform 250 transmits transaction ID 260 to data owner device 110 when encrypted record key 240B has been propagated to the blockchain. Using blockchain platform 250 to store encrypted record keys in the systems and methods disclosed herein has certain technical advantages over conventional systems. For example, using blockchain platform 250 to store and maintain record keys is more efficient for the user's device because less memory needs to be allocated to store and organize the record keys. The blockchain platform 250 also provides redundant storage of the user's record keys. In a system in which a user's keys are only stored locally, if the user's device is damaged or malfunctions, for example, and their stored keys could not be retrieved, all of their data would be lost. By contrast, the disclosed systems and methods use of blockchain platform 250 ensures secure, redundant, external storage of a user's record keys. Thus, if the user's device is damaged or malfunctions, they can still retrieve their record keys, such as by using another device.

Data owner device 110 encrypts the decrypted record 220B using record key 240A to generate encrypted record 220C. Data owner device 110 may perform this operation locally, using back-end processor 144 and/or key generating service 146 of data visibility control platform 140, or some combination of local and remote processing. Record key 240A may be used to re-encrypt decrypted record 220B before or after record key 240A is encrypted with data owner public key 210.

Data visibility control platform 140 may transmit encrypted record 220C, encrypted with record key 240A, to data intermediary 150. Data intermediary 150 may use record database 160 to store encrypted record 220C. In some embodiments, the data intermediary includes one or more record databases. In other embodiments, the data intermediary has access to and control over one or more record databases, such as cloud databases provided by a third-party or databases provided by a service provider (such as a healthcare service provider that may or may not be the same as the data consumer). This method enhances security to records stored in record database 160, including by not relying on the data intermediary to provide both visibility control and access and/or security controls. For example, by encrypting each record with its own user-generated record encryption key, even if record database 160 is successfully hacked, a bad actor would need to obtain every key in order to obtain access to the plaintext of every record of a given user. Further, when encrypted record key 240B is propagated to blockchain 250, it is stored on blockchain platform 250 and identifiable via transaction ID 260. As an added layer of security, record key 240A is propagated to the blockchain as encrypted record key 240B which can only be decrypted using data owner private key 230. Therefore, simply knowing transaction ID 260 to obtain encrypted record key 240B from blockchain platform 250 is still not enough to use record key 240A to decrypt encrypted record 220C. By contrast, in a known system in which all of the data records of a user are stored together, a successful hack can expose all of the user's records.

FIG. 3A depicts an example record stored on a blockchain, according to some embodiments. As depicted in FIG. 3A, blockchain platform 250 may be configured to store one or more transaction IDs 260. Each transaction ID 260 may correspond to cryptographic hash 222, encrypted record key 240B, and key identifier 224. For example, a first transaction ID 260.1, may correspond to: cryptographic hash 222.1, encrypted record key 240B.1, and key identifier 224.1. As discussed above, blockchain platform 250 may generate transaction ID 260 in response to receiving encrypted record key 240B. Cryptographic hash 222 may be used to determine whether the contents of decrypted record 220B have been modified. Key identifier 224 may be used to determine which key or key pair was used to encrypt encrypted record key 240B.

In some embodiments, there may be as many transaction IDs and encrypted record keys as there are encrypted records and cryptographic hashes associated with the data owner, e.g., transaction IDs 260.1-260.5 and record keys 240A.1-240A.5 corresponding to encrypted records 220C.1-220C.5 and cryptographic hashes 222.1-222.5. While FIG. 3A shows five transaction ID/cryptographic hash/encrypted record key/key identifier entries, a skilled artisan would have understood that storing tens, hundreds, thousands, millions, etc., of records associated with a data owner, which may be organized in any file structure, is within the scope of this disclosure. Some embodiments may store only transaction IDs and encrypted record keys, other embodiments store transaction IDs, cryptographic hashes, encrypted record keys, and key identifiers (as shown in FIG. 3A), or any combination thereof.

Figure 3B:
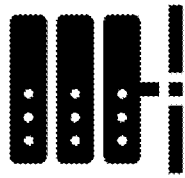
FIG. 3B depicts example storage a plurality of transaction IDs for records associated with a data owner, according to some embodiments.

FIG. 3B depicts example storage of a plurality of transaction IDs encrypted records associated with a data owner. As depicted in FIG. 3B, data intermediary 150 maintains transaction IDs 260 and the corresponding encrypted record 220C, encrypted with record key 240A. Data intermediary 150 may further maintain cryptographic hashes 222 corresponding to encrypted record 220C. As stated above, cryptographic hash 222 may be computed based on decrypted record 220B. Each transaction ID, such as transaction ID 260, is associated with a corresponding encrypted record, such as encrypted record 220C, and its accompanying cryptographic hash 222. For example, transaction ID 260.1 is associated with a specific encrypted record 220C.1 encrypted with record key 240A.1. Transaction ID 260.1 may be further associated with cryptographic hash 222.1, based on the decrypted version of encrypted record 220C.1. In some embodiments, there may be as many transaction IDs and record keys as there are encrypted records and cryptographic hashes associated with the data owner, e.g., transaction IDs 260.1-260.5 and record keys 240A.1-240A.5 corresponding to encrypted records 220C.1-220C.5 and cryptographic hashes 222.1-222.5. While FIG. 3B shows five transaction ID/encrypted record/cryptographic hash entries, a skilled artisan would have understood that storing tens, hundreds, thousands, millions, etc., of records associated with a data owner, which may be organized in any file structure, is within the scope of this disclosure. Some embodiments store only transaction IDs and encrypted records, other embodiments store transaction IDs, encrypted records, and cryptographic hashes (as shown in FIG. 3B).

The transaction ID and corresponding information for records encrypted by specific record keys 240A.1 are stored using data intermediary 150. Data intermediary 150 may store transaction IDs 260 and corresponding encrypted record 220C and (optionally) cryptographic hashes 222 locally or remotely. As discussed with reference to FIG. 1A, data intermediary may include or be associated with a database, such as record database 160. In some embodiments, data intermediary 150 may store transaction IDs 260, corresponding encrypted records 220C, and hashes 222 in record database 160.

In some embodiments, data intermediary 150 may store transaction IDs 260 (e.g., transaction IDs 260.1-260.5), encrypted records 220C (e.g., 220C.1-220C.5), and cryptographic hashes 222 (e.g., cryptographic hash 222.1-222.5). Data intermediary 150 stores the transaction ID(s) and associated encrypted record(s) and cryptographic hash(es), while the record key 240A (that is used to encrypt the record) is encrypted and stored on the blockchain platform 250 (e.g., as encrypted record key 240B of FIG. 2C). In some embodiments, one or more data intermediaries 150 may store the data owner's records. For example, a first data intermediary 150 may store transaction IDs 260.1-260.2 and corresponding encrypted records 220C.1-220C.2 and cryptographic hashes 222.1-222.2 and a second data intermediary 150 may store transaction IDs 260.3-260.5 and corresponding encrypted records 220C.3-220C.5 and cryptographic hashes 222.3-222.5.

Data intermediary 150 further enhances memory efficiency at the data owner's device because the data owner does not need to locally store the transaction IDs associated with their stored records. This is an added layer of security as record keys 240A are identified using the corresponding transaction ID 260. Data intermediary 150 stores both the transaction IDs 260 and encrypted records 220C. However, even with the transaction IDs 260 and/or encrypted records 220C, record keys 240A are only stored on the blockchain of blockchain platform 250 as encrypted record keys 240B. Encrypted record keys 240B were encrypted with data owner public key 210 and may only be decrypted using data owner private key 230. Therefore, if there was a security failure and a bad actor was able to access the transaction IDs 260 and/or encrypted records 220C, they would still be unable to decrypt record keys 240A without data owner private key 230.

For example, transaction ID 260.1 and encrypted record 220C.1 is associated with record key 240A.1. Record key 240A.1, in turn, is encrypted using data owner public key 210, and stored using blockchain platform 250. Data intermediary 150 may store the transaction ID 260.1 associated with encrypted record 220C.1 and record key 240A.1 such that data owner device may use the transaction ID 260.1 to retrieve encrypted record key 240B.1 from blockchain platform 250.

As will be discussed below, records at data intermediary 150 may be updated. As a result, a new cryptographic hash 222 may be calculated based on the updated record. In order to link the previous and modified record, the previous cryptographic hash 222 may be stored within the modified/updated version of the record. For example, when a new version of a record is created, a hash of the previous version of the record may be embedded in the new version of the record, which is then encrypted and stored according to the record-level encryption scheme disclosed herein.

FIG. 4A depicts an example process for providing a data consumer access to a record stored with record-level encryption, according to some embodiments. The data consumer may be the same or a different entity than the entity that created the record. For example, a medical specialist may create a record of a patient's visit, which is subsequently encrypted and stored using the techniques of FIGS. 2A-2C. Thereafter, the patient's primary care physician, insurance company, etc., may seek access to the patients record using the techniques of FIG. 4A.

Data consumer device 120 may identify a record, such as encrypted record 220C of FIG. 2C that is stored in record database 160. Data consumer device 120 may generate a request to access encrypted record 220C, such as encrypted request 410. The request may include the transaction ID (TID) of the desired record. In some embodiments, data consumer device 120 may not have access to the TID, and therefore not be able to include it within a request. Here, data consumer device 120 may include a description of information it is looking for within the request. For example, data consumer device 120 may be associated with a car insurance company, looking for medical records of a driver involved in a car accident. Here, the request may include details of the accident such as parties involved, date, time, and location. The request may further include purpose of use, requesting party identification, timestamp, and network through which the request was sent. In some embodiments, data visibility control platform 140, data intermediary 150, data owner device 110, or a combination thereof, may determine TIDs of records corresponding to the request. In some embodiments, an artificial intelligence or machine learning based search engine may be used to identify TIDs matching the request. TIDs matching the request may be sent to data consumer device 120. In some embodiments, only the TIDs may be sent to data consumer device 120 to ensure that the records are maximally protected. For example, descriptive record metadata, such as timestamp or record title, may not be provided to data consumer device 120.

A request may also include purpose of use. The purpose of use may include how the record or data in the record will be used or processed by data consumer device 120 and why access is needed. For example the request may include level of access that the data consumer seeks (such as read only, edit, etc.) and/or the reason why access is needed, e.g., a healthcare provider may need to access records to perform a health assessment or upload new records to a patient's file. In some embodiments, permission to edit an existing record generates a new, modified version of the record that includes the edits while maintaining a copy of the un-modified record. In other embodiments, permission to edit an existing record modifies the existing record without maintaining a copy of the un-modified record. The request may also include information that enables the data owner to help evaluate whether the request should be granted, such as information that identifies the party making the request, a timestamp associated with the request, the communication network through which the request was transmitted, to name a few non-limiting examples. For example, a data owner who was recently in a car accident may expect one or more requests to access certain records from their automobile insurance company and from the automobile insurance company of the other party to the accident. But the same data owner may not expect an unrelated or unknown entity to request access to those records. Such a request from an unknown entity may indicate that the request is fraudulent and should not be granted. In some embodiments, the data consumer may encrypt the request using data owner public key 210 such that only the data owner can decrypt and review the request (using data owner private key 230). In embodiments in which the data consumer and data owner maintain a shared private key (e.g., FIG. 2B), the request may be encrypted using the shared private key (e.g., private (shared) key 215A of FIG. 2B). The data consumer may also digitally sign (using its own private key such as data consumer private key 440) the request to enable the data owner to confirm that the request is from the data consumer by decrypting the request using the data consumer's public key, such as data consumer public key 420. Data visibility control platform 140 may provide data consumer device 120 with access to the data owner public key 210 when data owner device 110 grants access to data consumer device 120 to data owner's records identified by the submitted TIDs.

In some embodiments, data consumer device 120 may transmit encrypted request 410 to data intermediary 150. Data intermediary 150 may transmit encrypted request to data owner device 110. In some embodiments, data consumer device 120 may use data visibility control platform 140 to transmit encrypted request 410 to data owner device 110 via the user interface of front-end 142.

Data owner device 110 may decrypt encrypted request 410 using data owner private key 230 (or a private (shared) key, such as private (shared) key 215A in embodiments in which the date owner and data consumer maintain a shared private key). Data owner device 110 may identify encrypted record 220C and transaction ID 260 in the decrypted request. After decrypting the request, data owner device 110 may use transaction ID 260 identified in the decrypted request to retrieve encrypted record key 240B from blockchain platform 250. As described above with reference to FIG. 2C, blockchain platform 250 generates transaction ID 260 when data owner device 110 propagates encrypted record key 240B to blockchain platform 250. Blockchain platform 250 stores transaction ID 260, encrypted record key 240B, and a corresponding document hash (e.g., cryptographic hash 222) on the blockchain as a transaction. Blockchain platform 250 may further store key identifier 224 identifying the key or key-pair used by data owner device 110.

FIG. 4B depicts the continuation of the example process for providing data consumer access to a record stored with record-level encryption, according to some embodiments.

As described with reference to FIG. 4A, data owner device 110 may decrypt encrypted record key 240B with data owner private key 230 to retrieve record key 240A associated with the requested record. Data owner 110 may use key identifier 224 to determine that data owner private key 230 may be used to decrypt encrypted record key 240B. For example, data owner device 110 may maintain multiple public-private key pairs. Each key pair may have an identifier such as key identifier 224. Data owner device 110 may use the key or key-pair corresponding to the identifier (e.g., key identifier 224) returned by blockchain platform 250. Data owner then encrypts record key 240A using data consumer public key 420 to generate encrypted record key 430.

Data owner device 110 may receive data consumer public key 420 in a variety of ways, including in a uni-cast or broadcast message received from data consumer, visiting a website on which the key is published, and from key generating service 146, to name a few examples. As described in FIG. 1B, data consumer device may use back-end processor 144, key generating service 146, and entropy source 148 to generate a public and private key pair (e.g., data consumer public key 420 and data consumer private key 440.) In some embodiments, this data consumer device 120 may generate the cryptographic keys and key generating service 146 may store the public and private key pairs for later use, such as described in FIGS. 4A-C. In some embodiments, a third-party certificate authority may generate a public-private key pair for data consumer device 120. In some embodiments, data consumer device 120 may store generated encryption keys in a third-party key vault, such as a remote secure vault. In some embodiments, data consumer device 120 may store encryption keys in a cold storage system without internet access. Data owner device 110 may request access to data consumer public key 420 through data visibility control platform 140 via the user interface of front-end 142.

After generating encrypted record key 430, data owner device 110 may digitally sign encrypted record key 430 using data owner private key 230. The digital signature may allow the data intermediary (who may have access to data owner public key 210), and ultimately the data consumer, to demonstrate that the information was sent by the data owner. Data owner device 110 may then transmit encrypted record key 430 to data consumer device 120. In some embodiments, data owner device 110 may use the user interface of front-end 142 to transmit encrypted record key 430 to data consumer device 120. Data consumer device 120 may (when digitally signed) verify the digital signature using data owner public key 210 and decrypt encrypted record key 430 with data consumer private key 440. In some embodiments, this decryption is done locally on data consumer device 120. In other embodiments, data consumer device 120 may use back-end processor 144 and/or key generating service 146 provided by data visibility control platform 140 to decrypt encrypted record key 430. When data consumer device 120 decrypts encrypted record key 430, data consumer device 120 has access to record key 240A. As described above and with reference to FIG. 2C, encrypted record 220C was encrypted with record key 240A.

FIG. 4C depicts the continuation of the example process for providing data consumer access to a record stored with record-level encryption, according to some embodiments. As described with reference to FIGS. 4A and 4B, data consumer device 120 requests encrypted record 220C from data intermediary 150. The encrypted record 220C may be requested using the TID associated with encrypted record or any other information (e.g., title, date of record, general description of the record, to name a few examples) by which records are indexed in the data intermediary's database. In some embodiments, data intermediary 150 may confirm that the data owner has granted the requested permission to the data consumer (such as read, edit, etc.). The requested permission or level of access may be included in the request that the data consumer sends to the data owner. Data intermediary 150 may transmit encrypted record 220C from record database 160 to data consumer device 120.

Data consumer device 120 may decrypt encrypted record 220C using record key 240A. In some embodiments, such decryption is performed locally on data consumer device 120. In other embodiments, data consumer device 120 may use back-end processor 144 and/or key generating service 146 provided by data visibility control platform 140 to decrypt encrypted record 220C. By decrypting encrypted record 220C with record key 240A, requester device is able to access the plaintext of record 220B.

In some embodiments, data consumer device 120 may read, or read and edit, decrypted record 220B. In some embodiments, when editing a record, data consumer device 120 may read and edit the record and then send to data owner device 110 a request to store (to the records database via the data intermediary) a new, modified version of the record that contains the edits. Data consumer device 120 may use the process described in FIGS. 2A, 2B, and 2C to start the process required to save the new, modified version of the record while maintaining a copy of the unmodified version of the record. Additionally or alternatively, the framework may allow the data consumer device 120 to send the data owner device 110 a request to overwrite an existing record with the new, modified version of the record without maintaining a copy of the un-modified version of the record.

As shown and described throughout, all communications between data owner device 110 and data consumer device 120 may employ layers of encryption to prevent unauthorized access to the information and to authenticate (e.g., using digital signatures) the parties that are exchanging the information. Data owner private key 230 and requester private key 440 are kept secret by the data owner and the data consumer, respectively.

Figure 5:
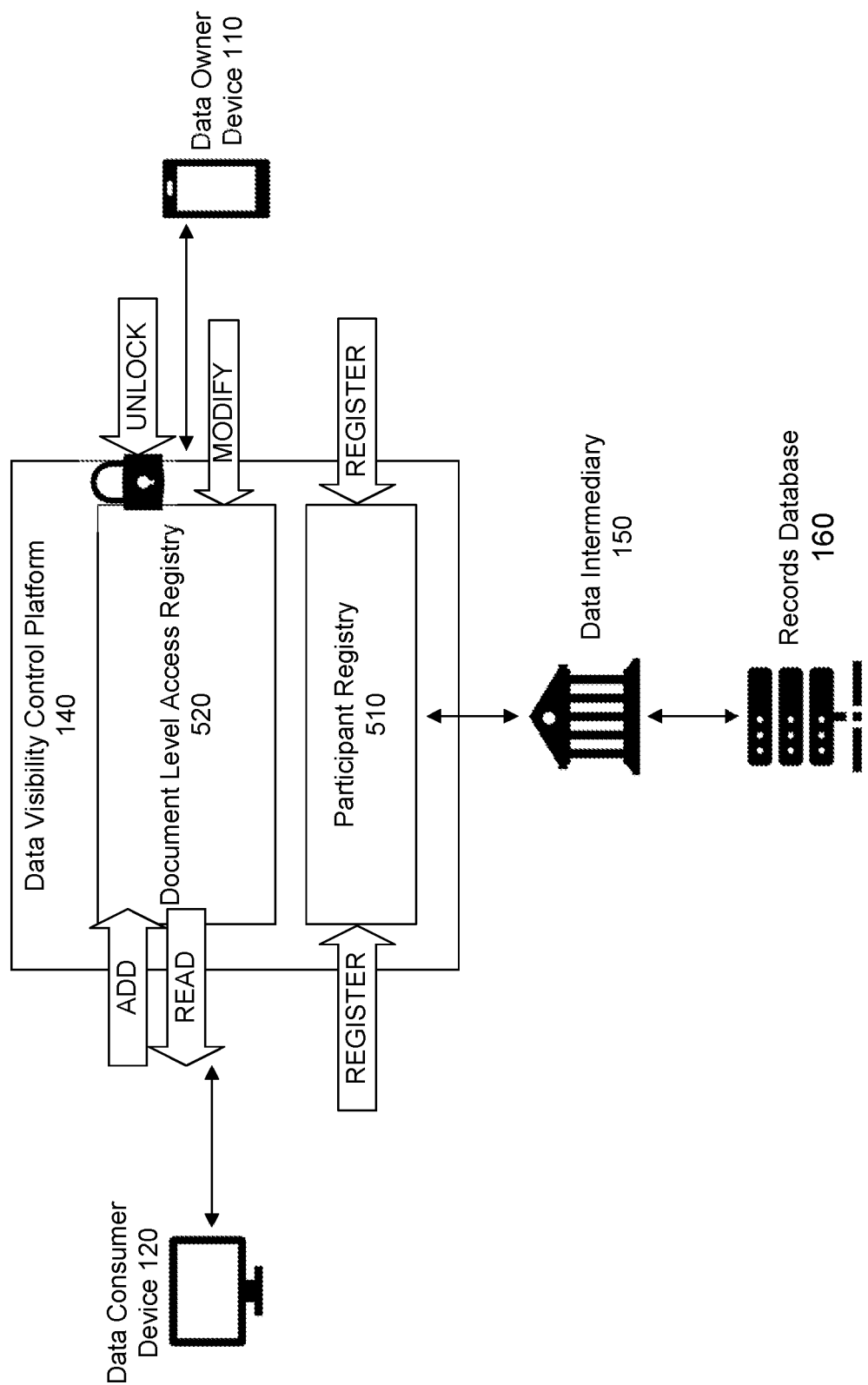
FIG. 5 depicts an example framework for data owner and requester registration for a record-level encryption scheme, according to some embodiments.

FIG. 5 depicts an example framework 500 for data owner and requester registration for a record-level encryption scheme, according to some embodiments. To encrypt and share documents on the record-level as shown and described in FIGS. 2A-4C, data owners and requesters may register with data visibility control platform 140. During registration, data visibility control platform 140 may confirm the identities of the individuals and/or entities registering as data owners and/or data users/requesters. A skilled artisan would understand that data owners may be data users/requesters in some circumstances, and data users/requesters may be data owners in some circumstances. For example, in a medical provider-patient relationship, both parties may own sensitive or confidential data that the other party may seek access to. In some embodiments, participant registry 510 stores data owners and requesters who have registered with data visibility control platform 140.

As shown in FIG. 5, data owners and requesters may communicate with data intermediary 150 regarding access of records, as described with reference to FIGS. 2A-4C. Data intermediary 150 may communicate with data visibility control platform 140 to ensure that data owners and requester are registered. For particular records, data intermediary 150 may confirm that data owner device 110 has granted access to consumer device 120 for a given record.

Document level access registry 520 may track access for records associated with each data owner. Data owner device 110 may grant, deny, reject, and/or revoke access to records managed by data intermediary 150 and stored (encrypted with the methods described above) in record database 160 via data visibility control platform 140. If a data owner decides they no longer want to grant access to a given requester, they may revoke access via document level access registry 520 of data visibility control platform 140. For example, a requester may be a medical provider with access to data owner's patient records managed by data intermediary 150 and stored in record database 160. Data owner may transfer their medical care to a different medical provider. Data owner device 110 may access data visibility control platform 140 to revoke the access of the previous medical provider for all records within data owner's patient file. Data owner device 110 may be further configured to deny (e.g., reject) access requested by a requester. For example, a requester (e.g., data consumer device 120) may send a request for a record belonging to a data owner associated with data owner device 110. In response, data owner device 110 may deny the request. For example, data owner device 110 may interface with front-end 142 to deny the request. The data owner may deny the request for any reason such as: (1) a time of the request; (2) an identity of the requester; (3) a location the request originated from; or (4) a reason the request was made. As a result, data visibility control platform 140 may prevent the request from accessing the record.

Data owner device 110 may also grant access to data owner's patient records to the new medical provider. At any time, data owner may choose to grant, revoke, deny (e.g., reject), or restrict access (such as changing access rights from read and edit to read only). This de-centralizes the access to data owners' records by giving them direct control of the visibility of their records (the contents of which are encrypted and thus are not visible to data intermediary 150). Data owners do not have to communicate to data intermediary 150 their desire to change data visibility and consent to access their records. Data intermediary 150 may still have privacy and security protocols for managing and storing data (with encryption layers implemented by data intermediary 150 in addition to the ones described).

Data owner device 110 may also be able to modify data at data intermediary 150. In some embodiments, data owner device 110 may add information to records created by data consumer device 120. For example, a record created by data consumer device 120 may include a section listing exercise or nutrition information linked to the data owner. Here, data owner device 110 may access the record and input updated exercise and/or nutrition information. Data owner device 110 may change information in records created by data consumer device 120. For example, data consumer device 120 may have created a record and included an incorrect address or date of birth for the data owner. In response, data owner device 110 may access the record and correct the information. In some embodiments, data owner device 110 may delete part of a record, or an entire record.

Data intermediary 150 may authenticate the data owner attempting to modify the record prior to allowing the operation. For example, the data may be required to submit a password, biometric input, or any other form of authentication via data owner device 110 to data intermediary 150. In some embodiments, the data owner may be required to perform multi-factor authentication such as inputting a password, and then entering a code sent to a phone number or email associated with data owner device 110. In some embodiments, the request may be authenticated by the data owner providing a digital signature. For example, the data owner may use their private key (e.g., data owner private key 230) to digitally sign and authenticate the request. Once authenticated, data intermediary 150 may perform the requested action. In some embodiments, all modifications may require authentication. In other embodiments, data intermediary 150 may be configured to require authentication for certain actions. For example, data intermediary 150 may require authentication when data owner device 110 attempts to delete part of, or an entire record.

In some embodiments, cryptographic hashes may be used to track changes through different versions of a record. When a record is being edited, a hash of the current version of the record may be computed or the previously computed hash of the current version of the record may be retrieved. As discussed above, data intermediary 150 may store a cryptographic hash of each record in association with the encrypted record, such as cryptographic hash 222.1 associated with encrypted record 220C.1 of FIG. 3B. As shown in FIG. 3A, the cryptographic hash may also be stored on the blockchain (e.g., blockchain platform 250). When the record is edited, the hash of the current version of the record (that is, the version of the record that is to be edited) may be appended to, or embedded within, the edited version of the record. As a result, each new version of a record may include a hash of the immediately previous version of the record, creating a sequential linking of versions of the record. For example, a data owner may use data owner device 110 to edit a record. In doing so, the data owner may compute or retrieve the hash of the current version of the record and create the edited version of the record to which the hash is appended or embedded within. The data owner device 110 will then apply the procedure outlined in FIG. 2C to the edited version of the record. The data consumer may follow the same procedure (once authorized by the data owner) to edit a record.

Data owner device 110 may also manage record access based on record versions. For example, data owner device 110 may grant access to the first version of a record to data consumer device 120, but not the second version. This may be useful if the record owner, wishes to grant two parties partial access to the record. For example, the first record version may be created by the record owner's first medical provider. The record owner may subsequently switch providers. As a result, data owner device 110 associated with the record owner may generate a new version of the record. The new version may be associated with a new hash value. Data owner device 110 may then limit the first provider's access to the first version by associating their access with the first version's hash value. Additionally, data owner device 110 may grant the new provider access to the second version of the record by linking the new provider's access with the second version's hash value. In some embodiments, the hash may be cryptographic hash 222. For example, document level access registry 520 may store key value pairs, where the key is cryptographic hash 222 corresponding to a record version, and the value is the entity (e.g., data consumer device 120) with access to that version of the record.

Data visibility control platform 140 may be accessed via a web browser, hybrid or native web application, and/or application programming interface (API), etc., which is accessible by data owner device 110 and/or data consumer device 120. Data visibility control platform 140 may provide a graphical user interface (GUI) via front-end 142 that allows data owner device 110 to, in real-time, quickly and clearly grant, deny, and revoke access to requesters.

Figure 6A:
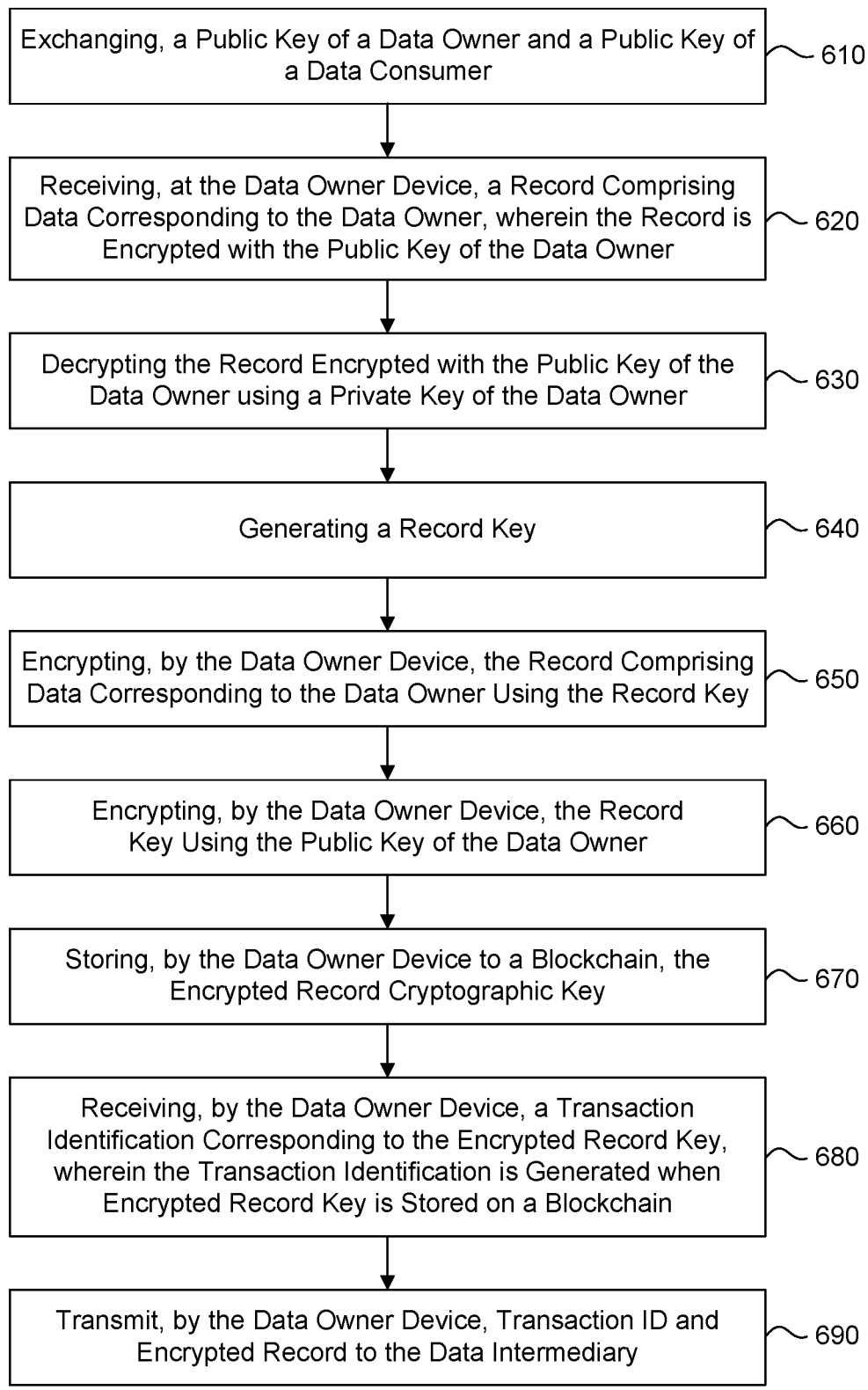
FIG. 6A-6B depict a flowchart illustrating a method for generating and storing a record, according to some embodiments.
Figure 6B:
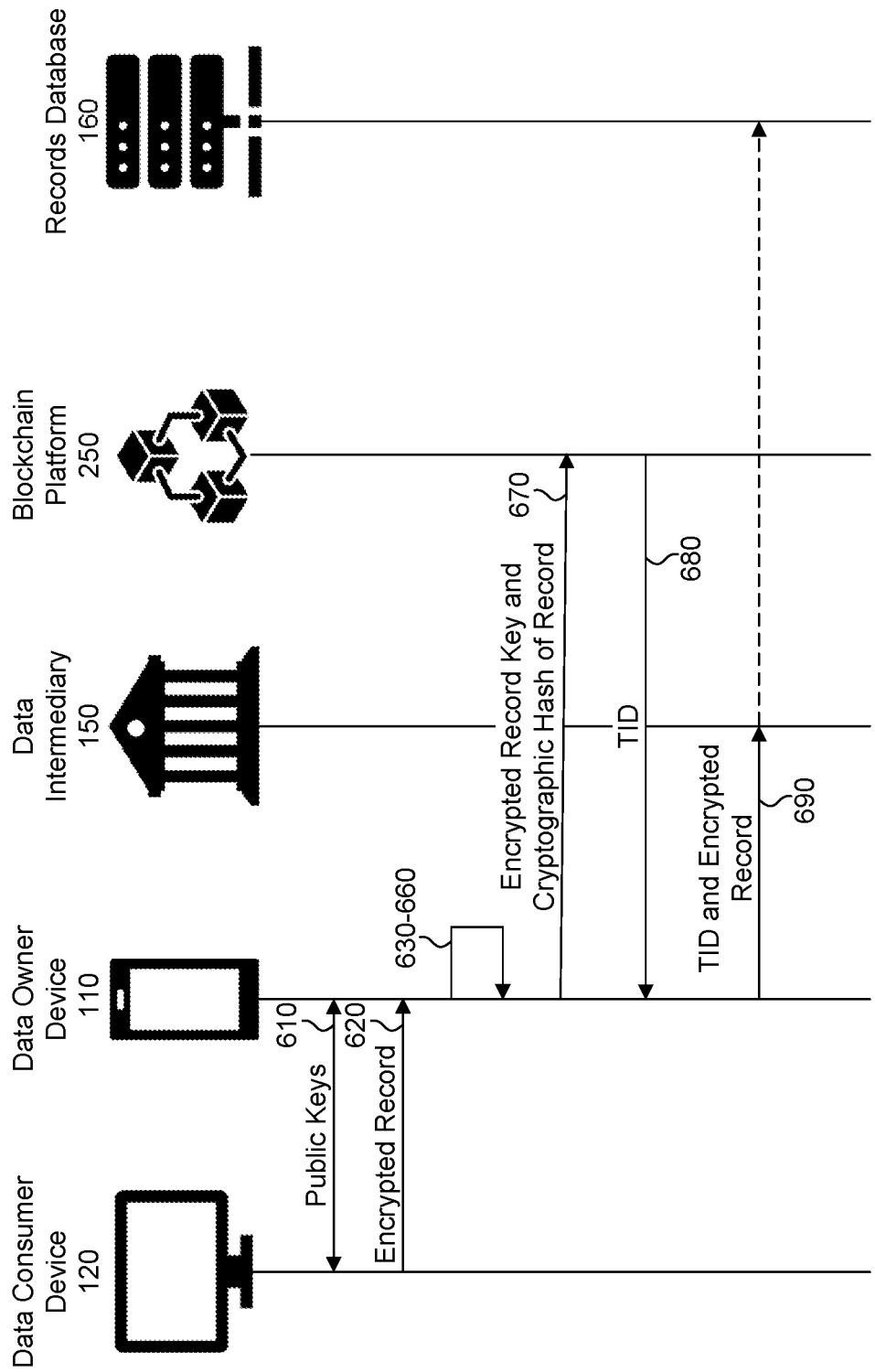

FIGS. 6A-6B depict a flowchart illustrating a method 600 for record-level encryption for a newly generated record from the point-of-view of data owner device 110, according to some embodiments. Method 600 shall be described with reference to FIGS. 1, 2A, 2B, 2C, 4A, 4B, and 4C; however, method 600 is not limited to that example embodiment.

In an embodiment, data owner device 110, data consumer device 120, data visibility control platform 140, and/or data intermediary 150 may utilize method 600 to provide record-level encryption for records of data owner or newly generated records. Records may be managed by data intermediary 150 and stored in record database 160. The record-level encryption described in method 600 may allow a data owner to have direct control over the visibility of their records, while allowing data intermediary 150 and/or record database 160 to manage security and privacy protocols. The foregoing description will describe an embodiment of the execution of method 600 with respect to data owner device 110, data consumer device 120, data visibility control platform 140, data intermediary 150, and/or record database 160. While method 600 is described with reference to data visibility control platform 140, method 600 may be executed on any computing device, such as, for example, the computer system described with reference to FIG. 8 and/or processing logic that may comprise hardware (e.g., circuitry, dedicated logic, programmable logic, microcode, etc.), software (e.g., instructions that are stored in non-transitory computer-readable memory and that are executable using one or more processing devices), or a combination thereof.

It is to be appreciated that not all steps may be needed to perform the disclosure provided herein. Further, some of the steps may be performed simultaneously, or in a different order than shown in FIGS. 6A-6B, as will be understood by a person of ordinary skill in the art.

At 610, the data owner and the data consumer may generate public-private key pairs and may exchange public keys. As explained above, public keys may be exchanged by direct messages, broadcast messages, publishing the keys to a public forum or website, etc. In one example, data owner device 110 may use the user interface of front-end 142 to transmit data owner public key 210 to data consumer device 120, and vice versa. Data owner device 110 may use back-end processor 144, key generating service 146, and entropy source 148 of data visibility control platform 140 to generate data owner public key 210 and data owner private key 230. Similarly, data consumer device 120 may use back-end processor 144, key generating service 146, and entropy source 148 of data visibility control platform 140.

As described in FIGS. 2A-2C, data consumer device 120 may generate a record comprising data of the data owner. In some embodiments, a record may be a file in a computer readable format or another form of electronically stored data. Data consumer device 120 may encrypt the record using data owner public key 210.

At 620, data owner device 110 may receive the record that is encrypted using the data owner's public key, such as data owner public key 210 of FIG. 2A. In some embodiments, data owner device 110 may receive the encrypted record from data intermediary 150.

In some embodiments, data consumer device 120 may upload the record encrypted with data owner public key 210 to data intermediary 150 via network 130. Data intermediary 150 may transmit the encrypted record to data owner device 110. In some embodiments, data consumer device 120 may use data visibility control platform 140 to upload the encrypted record to data intermediary 150 and data visibility control platform 140 may also transmit the encrypted record to data owner device 110.

At 630, the data owner may decrypt the encrypted record using the data owner's private key, such as data owner private key 230 of FIG. 2A. Data owner device 110 may use data owner private key 230 to perform this decryption locally using hardware and/or software on data owner device 110 or may use the back-end processor 144 and/or key generating service 146 to decrypt the encrypted record with data owner private key 230. The data owner may also generate a cryptographic hash of the record, which may be used for future authentication of the record.

At 640, the data owner generates a record key associated with the record. Data owner device 110 may generate record keys, such as record key 240A of FIG. 2C, locally using hardware and/or software on data owner device 110 or may use back-end processor 144, key generating service 146, and/or entropy source 148 of data visibility control platform 140 to generate record keys. The data owner may generate a record key for each record of the data owner. In some embodiments, the data owner may also generate a new record key each time a record is edited and repeat the process described with reference to FIG. 2A-2C to upload a new encrypted record containing the edits, while data intermediary 150 stores each version of the record.

At 650, the data owner encrypts the record comprising data corresponding to the data owner using the record key. In some embodiments, data owner device 110 may use back-end processor 144 and/or key generating service 146 provided by data visibility control platform 140 to encrypt the record with record key 240A, e.g., the record key.

At 660, the data owner encrypts the record key using the public key of the data owner, such as data owner public key 210 of FIG. 2C, to generate an encrypted record key, such as encrypted record key 240B of FIG. 2C. In some embodiments, data owner device 110 may encrypt record key with data owner public key 210 locally using hardware and/or software on data owner device 110 or may encrypt the record key via back-end processor 144 and/or key generating service 146 provided by data visibility control platform 140.

At 670, the data owner may store the encrypted record key and a cryptographic hash (e.g., cryptographic hash 222) of the record in a blockchain. In some embodiments, data owner device 110 may propagate encrypted record key 240B to blockchain platform 250. Data owner may further store an identifier corresponding to the public-private key pair (e.g., data owner public key 210 and data owner private key 230). The identifier may be key identifier 224.

At 680, the data owner may receive a transaction ID corresponding to the encrypted record key, wherein the transaction ID is generated when encrypted record key is stored on a blockchain. More specifically, the blockchain may generate the transaction ID and store the transaction ID, the encrypted record key, and a cryptographic hash of the record in a block of the blockchain.

At 690, the data owner transmits at least the transaction ID and encrypted record to the data intermediary, which stores them in the records database. In some embodiments, a data owner storage service may also record that transaction ID 260 is associated with encrypted record key 240B and record key 240A. In some embodiments, there may be a plurality of records associated with the data owner. Therefore, there may be a plurality of record keys 240A, corresponding encrypted record keys 240B, and corresponding transaction IDs 260. A data owner storage service may store each transaction ID 260 and the associated record identification, record keys 240A, and/or encrypted record keys 240B.

In some embodiments, data owner device may transmit the encrypted record, encrypted with record key 240A, to data intermediary 150. Data intermediary 150 may use record database 160 to store the encrypted record.

Figure 7:
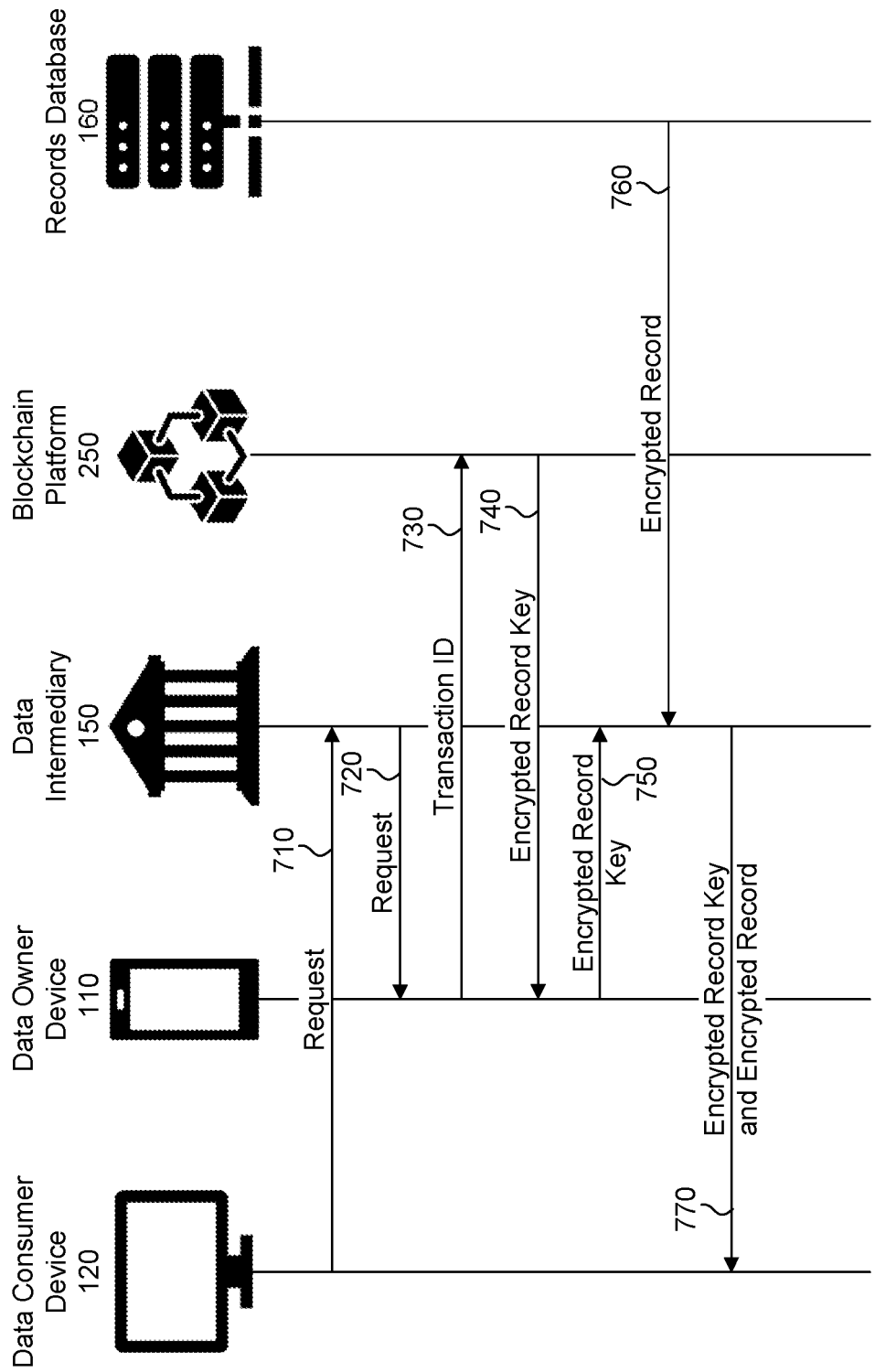
FIG. 7 is a process flow diagram illustrating a process for accessing a record, according to some embodiments.

FIG. 7 depicts a process flow diagram illustrating a method 700 for record-level encryption for reading and/or editing a record. Method 700 shall be described with reference to FIGS. 1, 2A, 2B, 2C, 4A, 4B, and 4C; however, method 700 is not limited to that example embodiment.

In an embodiment, data visibility control platform 140 may utilize method 700 to provide record-level encryption for records of data owner for accessing records of a data owner. In some embodiments, records that are accessed may be edited and stored as a new encrypted record, data owner device 110 and data consumer device 120 may utilize FIGS. 2A-2C and FIG. 6A-6B to store newly generated, encrypted records. Encrypted records may be managed by data intermediary 150 and stored in record database 160. The record-level encryption described in method 700 may allow a data owner to have direct control over the visibility of their records, while allowing data intermediary 150 and/or record database 160 to manage security and privacy protocols. In some embodiments, the data consumer discussed in method 700 may be the party that generated the record (e.g., the data consumer described in FIG. 6) or may be a different party. For example, a health care professional may generate a record for a patient's file after a visit. The healthcare professional may use method 600 to generate the file. A different data consumer, e.g., a health insurance provider, may need to access the data owner's record generated by the healthcare professional. The method described in FIG. 7 may be used by any data consumer who has been given access to view the data owner's records to request access to a specific record and receive that record from the data intermediary. While method 700 is described with reference to data visibility control platform 140, method 700 may be executed on any computing device, such as, for example, the computer system 800 described with reference to FIG. 8 and/or processing logic that may comprise hardware (e.g., circuitry, dedicated logic, programmable logic, microcode, etc.), software (e.g., instructions executing on a processing device), or a combination thereof.

It is to be appreciated that not all steps may be needed to perform the disclosure provided herein. Further, some of the steps may be performed simultaneously, or in a different order than shown in FIG. 7, as will be understood by a person of ordinary skill in the art.

At 710, data consumer device 120 may generate a request. The request may comprise a message indicating the data consumer wants to access an encrypted record of the data owner stored in record database 160. The request may identify an encrypted record with the transaction ID (e.g., transaction ID 260.) The request may also include identifying information of data consumer device 120 and/or the data owner as well as the purpose of use for the encrypted record and its data to allow the data consumer to evaluate whether the request should be granted. For example, this could include identifying information of the data consumer and/or data consumer device 120, a timestamp associated with the request, and/or a digital signature added to the encrypted request, to name a few non-limiting examples. In some embodiments, data consumer device 120 may encrypt the request using data owner public key 210. As explained above, public keys may be exchanged by direct messages, broadcast messages, publishing the keys to a public forum or website, etc.

Data consumer device 120 may transmit the encrypted request to data owner device 110 via data intermediary 150. In one example, data consumer device 120 may use the user interface of front-end 142 to transmit the request to data owner device 110. Data consumer device 120 may also transmit the encrypted request to the data owner via a network, without routing the request through the data intermediary 150.

At 720, data owner device 110 may receive the request generated by data consumer device 120. In some embodiments, data owner device 110 may receive the encrypted request from data intermediary 150 via network 130. Data owner device 110 may decrypt the encrypted request. Data owner device 110 may decrypt the encrypted request including transaction ID using the data owner private key. As described above, the encrypted record key used to decrypt the encrypted record stored in record database 160 is stored on blockchain platform 250. The encrypted record key may be identified and retrieved by data owner device 110 using transaction ID 260 identified in the request. For example, the request may identify transaction ID 260.1, which corresponds to encrypted record 220C.1 and record key 240A.1. Record key 240A.1 may be stored on blockchain platform as encrypted record key 240B.1.

At 730, data owner device 110 may request the encrypted record key from blockchain platform 250. Data owner device 110 may identify the encrypted record key using the corresponding transaction ID identified in the request from data consumer device 120. As described above, when the encrypted record is generated, as described in FIG. 6 using method 600, the record stored in record database 160 is encrypted using a record key. The record key is encrypted using the data owner's public key and stored via blockchain platform 250.

At 740, data owner device 110 may receive the encrypted key from blockchain platform 250. Data owner device 110 may also receive the cryptographic hash of the record from blockchain platform 250. The cryptographic hash may be cryptographic hash 222. Data owner device 110 may further receive the key identifier from blockchain platform 250. The key identifier may be key identifier 224. Data owner device 110 may use the data owner private key to decrypt the encrypted record key. For example, data owner device 110 may use data owner private key 230 to decrypt encrypted record key 240B to retrieve record key 240A. Data owner device 110 may determine that data owner private key 230 is capable of decrypting encrypted record key 240B based on key identifier 224. For example, data owner device 110 may include a lookup table or other data structure linking key identifier 224 to data owner public key 210 and data owner private key 230. In order for data consumer device 120 to access the encrypted record, data owner device may transmit the record key to data consumer device 120. To securely transmit the record key, data owner device 110 may encrypt the record key using the data consumer public key. As explained above, public keys may be exchanged by direct messages, broadcast messages, publishing the keys to a public forum or website, etc. For example, data owner device 110 may encrypt record key 240A using data consumer public key 420. Encrypted record key 430 may be encrypted using data consumer public key 420.

At 750, data owner device 110 may transmit the encrypted record key to data consumer device 120 via data intermediary 150. In some embodiments, data owner device 110 may include a digital signature with encrypted record key 430. This may allow data intermediary 150 and/or back-end processor 144 of data visibility platform 140 to verify the data owner's identity. The data owner device 110 may use front-end 142 of data visibility control platform 140 to transmit the encrypted record key to data consumer vice 120 via data intermediary 150. Included with the encrypted record key may also be a request to retrieve the encrypted record for data consumer device 120. The encrypted record may be identified using the transaction ID that was identified in the request sent to data owner device 110 at 710.

At 760, data intermediary receives the encrypted record key and request to retrieve the encrypted record from record database 160 from data owner device 110. Data intermediary 150 may retrieve the encrypted record from record database 160. For example, data intermediary may retrieve encrypted record 220C.1 based on the included transaction ID 260.1.

At 770, data consumer device 120 may receive the encrypted record key and encrypted record from data intermediary 150. Data consumer device 120 may decrypt the encrypted record key using the data consumer private key to obtain the record key. Data consumer device 120 may then use the record key to decrypt the encrypted record and obtain the record corresponding to the transaction ID identified in the request from data consumer device 120 at 710. For example, data consumer device 120 may decrypt encrypted record key 430 using data consumer private key 440 to obtain record key 240A. Data consumer device 120 can also use the digital signature, when present, to confirm that the record key was provided by the data owner. Data consumer device 120 may decrypt encrypted record 220C using corresponding record key 240A to obtain the plaintext of the record identified in the request.

Figure 8:
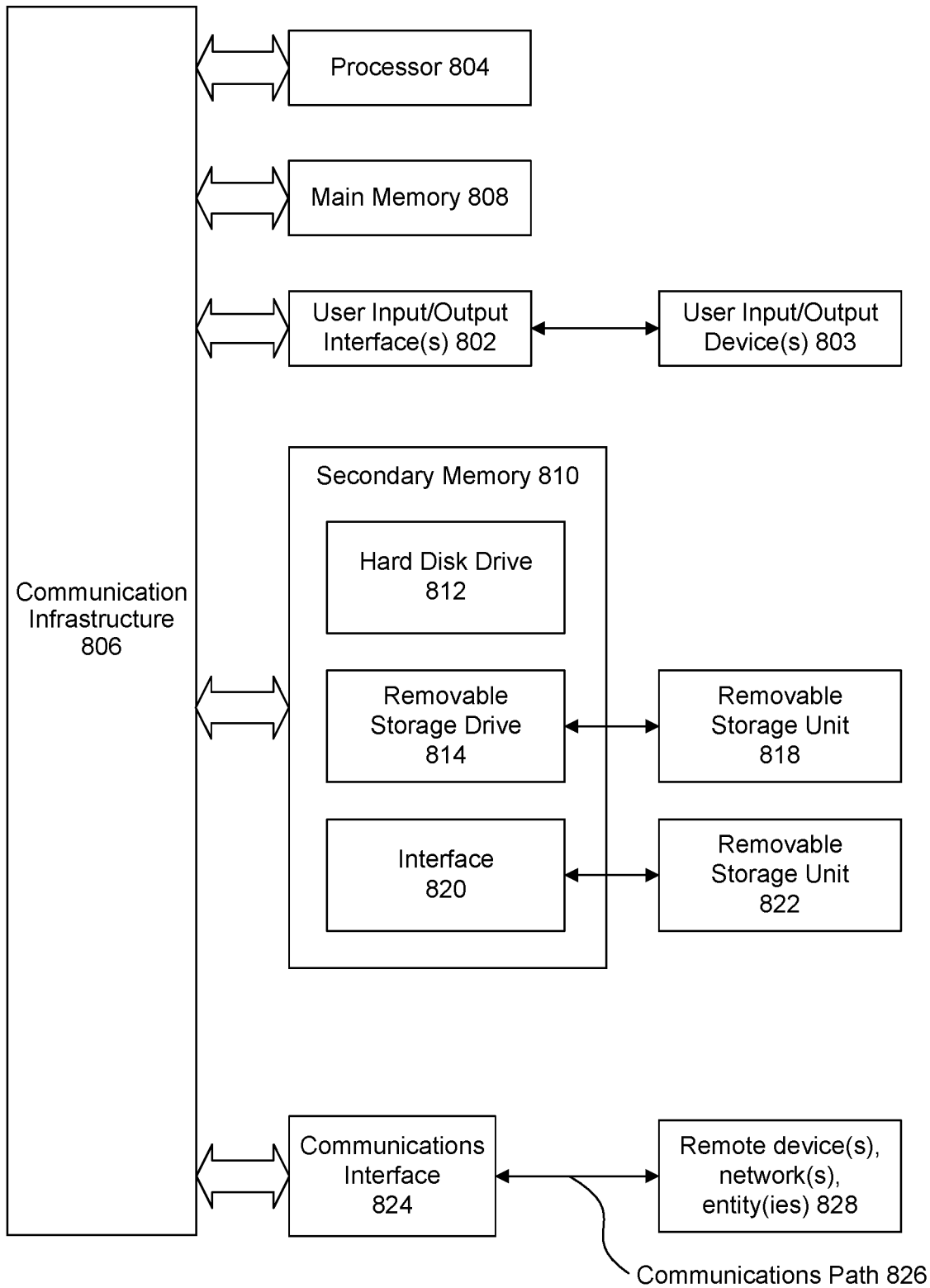
FIG. 8 is a block diagram of an example computer system useful for implementing various embodiments.

Various embodiments may be implemented, for example, using one or more computer systems, such as computer system 800 shown in FIG. 8. One or more computer systems 800 may be used, for example, to implement any of the embodiments discussed herein, as well as combinations and sub-combinations thereof.

Computer system 800 may include one or more processors (also called central processing units, or CPUs), such as a processor 804. Processor 804 may be connected to a bus or communication infrastructure 806.

Computer system 800 may also include user input/output device(s) 803, such as monitors, keyboards, pointing devices, etc., which may communicate with communication infrastructure 806 through user input/output interface(s) 802.

One or more of processors 804 may be a graphics processing unit (GPU). In an embodiment, a GPU may be a processor that is a specialized electronic circuit designed to process mathematically intensive applications. With capabilities of general-purpose computing on graphics processing units (GPGPU), the GPU may be useful in various other applications. The GPU may have a parallel structure that is efficient for parallel processing of large blocks of data, such as mathematically intensive data common to computer graphics applications, images, videos, vector processing, array processing, etc., as well as cryptography (including brute-force cracking), generating cryptographic hashes or hash sequences, solving partial hash-inversion problems, and/or producing results of other proof-of-work computations for some blockchain-based applications, for example.

Computer system 800 may also include a main or primary memory 808, such as random access memory (RAM). Main memory 808 may include one or more levels of cache. Main memory 808 may have stored therein control logic (i.e., computer software) and/or data.

Computer system 800 may also include one or more secondary storage devices or memory 810. Secondary memory 810 may include, for example, a hard disk drive 812 and/or a removable storage device or drive 814. Removable storage drive 814 may be a floppy disk drive, a magnetic tape drive, a compact disk drive, an optical storage device, tape backup device, and/or any other storage device/drive.

Removable storage drive 814 may interact with a removable storage unit 818. Removable storage unit 818 may include a computer usable or readable storage device having stored thereon computer software (control logic) and/or data. Removable storage unit 818 may be a floppy disk, magnetic tape, compact disk, DVD, optical storage disk, and/any other computer data storage device. Removable storage drive 814 may read from and/or write to removable storage unit 818.

Secondary memory 810 may include other means, devices, components, instrumentalities or other approaches for allowing computer programs and/or other instructions and/or data to be accessed by computer system 800. Such means, devices, components, instrumentalities or other approaches may include, for example, a removable storage unit 822 and an interface 820. Examples of the removable storage unit 822 and the interface 820 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 800 may further include a communication or network interface 824. Communication interface 824 may enable computer system 800 to communicate and interact with any combination of external devices, external networks, external entities, etc. (individually and collectively referenced by reference number 828). For example, communication interface 824 may allow computer system 800 to communicate with external or remote devices 828 over communications path 826, which may be wired and/or wireless (or a combination thereof), and which may include any combination of LANs, WANs, the Internet, etc. Control logic and/or data may be transmitted to and from computer system 800 via communication path 826.

Computer system 800 may also be any of a personal digital assistant (PDA), desktop workstation, laptop or notebook computer, netbook, tablet, smart phone, smart watch or other wearable, appliance, part of the Internet-of-Things, and/or embedded system, to name a few non-limiting examples, or any combination thereof.

Computer system 800 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 900 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 800, main memory 808, secondary memory 810, and removable storage units 818 and 822, as well as tangible articles of manufacture embodying any combination of the foregoing. Such control logic, when executed by one or more data processing devices (such as computer system 800), may cause such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 8. In particular, embodiments may operate with software, hardware, and/or operating system implementations other than those described herein.

It is to be appreciated that the Detailed Description section, and not any other section, is intended to be used to interpret the claims. Other sections may set forth one or more but not all example embodiments as contemplated by the inventor(s), and thus, are not intended to limit this disclosure or the appended claims in any way.

While this disclosure describes example embodiments for example fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries may be defined as long as the specified functions and relationships (or equivalents thereof) are appropriately performed. Also, alternative embodiments may perform functional blocks, steps, operations, methods, etc. using orderings different than those described herein.

References herein to "one embodiment," "an embodiment," "an example embodiment," "some embodiments," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

Additionally, some embodiments can be described using the expression "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described example embodiments, but should be defined only in accordance with the following claims and their equivalents.

We claim:

1. A method comprising:

generating, by a data owner device of a data owner, a first key identifier corresponding to a first public-private key pair of the data owner, wherein the first public-private key pair comprises a first public key of the data owner and a first private key of the data owner;

generating, by the data owner device, a second key identifier corresponding to a second public-private key pair of the data owner, wherein the second public-private key pair comprises a second public key of the data owner and a second private key of the data owner;

receiving, at the data owner device via a communications network, a record comprising data of the data owner, wherein the record is encrypted using the first public key of the data owner;

decrypting, by the data owner device, the record using the first private key of the data owner;

generating, by the data owner device, a record key;

encrypting, by the data owner device, the record using the record key;

encrypting, by the data owner device, the record key using the first private key of the data owner;

providing, by the data owner device via the communications network, the encrypted record key and the first key identifier to a storage device for storage, wherein the storage device is remote from the data owner device;

receiving, by the data owner device via the communications network, a transaction identification corresponding to the encrypted record key and the first key identifier, wherein the transaction identification is generated when the encrypted record key and the first key identifier are stored on the storage device;

providing, by the data owner device via the communications network, the record encrypted with the record key to a data intermediary for storage at the data intermediary, wherein the data intermediary is remote from the data owner device and the storage device;

receiving, by the data owner device via the communications network, a request from a data consumer to access the record, wherein the request comprises at least the transaction identification and the request is encrypted with the second public key of the data owner;

decrypting, by the data owner device, the request using the second private key of the data owner;

retrieving, by the data owner device from the storage device via the communications network, the encrypted record key corresponding to the transaction identification;

decrypting, by the data owner device, the encrypted record key using the first private key, wherein the data owner device identifies the first private key based on the first key identifier associated with the transaction identification;

encrypting, by the data owner device, the record key using a public key of the data consumer; and transmitting, by the data owner device via the communications network, the record key encrypted using the public key of the data consumer to a data consumer device.

2. The method of claim 1, further comprising:

receiving, by the data owner device via the communications network, a second request to access the record from the data consumer device, wherein the second request comprises the transaction identification and the second request is encrypted with the first public key of the data owner;

decrypting, by the data owner device, the second request to obtain the transaction identification using the first private key; and retrieving, by the data owner device from the storage device via the communications network, the encrypted record key corresponding to the transaction identification.

3. The method of claim 2, further comprising:

decrypting, by the data owner device, the encrypted record key using the first private key, wherein the data owner device identifies the first private key based on the first key identifier;

encrypting, by the data owner device, the record key using the public key of the data consumer; and transmitting, by the data owner device via the communications network, the record key encrypted using the public key of the data consumer to the data consumer.

4. The method of claim 3, further comprising:

applying a digital signature, by the data owner device, to the record key encrypted using the data consumer public key before transmitting the record key encrypted using the data consumer public key to the data consumer.

5. The method of claim 2, further comprising: denying access to the record, by the data owner device, based at least on a time the second request was generated or an identity of the data consumer.

6. The method of claim 2, wherein the data owner is a patient and the data consumer is a medical provider.

7. The method of claim 1, wherein prior to encrypting the record using the record key, the method further comprises generating, by the data owner device, a cryptographic hash of the record.

8. The method of claim 7, further comprising:

providing, by the data owner device via the communications network, the the cryptographic hash to the storage device for storage in association with the record key and the transaction identification.

9. A non-transitory computer-readable memory having instructions stored thereon that, when executed by at least one computing device, cause the at least one computing device to perform operations comprising:

generating, by a data owner device of a data owner, a first key identifier corresponding to a first public-private key pair of the data owner, wherein the first public-private key pair comprises a first public key of the data owner and a first private key of the data owner;

generating, by the data owner device, a second key identifier corresponding to a second public-private key pair of the data owner, wherein the second public-private key pair comprises a second public key of the data owner and a second private key of the data owner;

receiving, at the data owner device via a communications network, a record comprising data of the data owner, wherein the record is encrypted using the first public key of the data owner;

decrypting, by the data owner device, the record using the first private key of the data owner;

generating, by the data owner device, a record key;

encrypting, by the data owner device, the record using the record key;

encrypting, by the data owner device, the record key using the first private key of the data owner;

providing, by the data owner device via the communications network, the encrypted record key and the first key identifier to a storage device for storage on the storage device, wherein the storage device is remote from the data owner device;

receiving, by the data owner device via the communications network, a transaction identification corresponding to the encrypted record key and the first key identifier, wherein the transaction identification is generated when the encrypted record key and the first key identifier are stored on the storage device;

providing, by the data owner device via the communications network, the record encrypted with the record key to a data intermediary for storage at the data intermediary, wherein the data intermediary is remote from the data owner device and the storage device;

receiving, by the data owner device via the communications network, a request from a data consumer to access the record, wherein the request comprises at least the transaction identification and the request is encrypted with the second public key of the data owner;

decrypting, by the data owner device, the request using the second private key of the data owner;

retrieving, by the data owner device from the storage device via the communications network, the encrypted record key corresponding to the transaction identification;

decrypting, by the data owner device, the encrypted record key using the first private key, wherein the data owner device identifies the first private key based on the first key identifier associated with the transaction identification;

encrypting, by the data owner device, the record key using a public key of the data consumer; and transmitting, by the data owner device via the communications network, the record key encrypted using the public key of the data consumer to a data consumer device.

10. The non-transitory computer-readable memory of 9, wherein the operations further comprise:

receiving, by the data owner device via the communications network, a second request to access the record from the data consumer device, wherein the second request comprises the transaction identification and the second request is encrypted with the first public key of the data owner;

decrypting, by the data owner device, the second request to obtain the transaction identification using the first private key; and retrieving, by the data owner device from the storage device via the communications network, the encrypted record key corresponding to the transaction identification.

11. The non-transitory computer-readable memory of claim 10, wherein the operations further comprise:
    decrypting, by the data owner device, the encrypted record key using the first private key, wherein the data owner device identifies the first private key based on the first key identifier;
    encrypting, by the data owner device, the record key using the public key of the data consumer; and
    transmitting, by the data owner device via the communications network, the record key encrypted using the public key of the data consumer to the data consumer.

12. The non-transitory computer-readable memory claim 11, wherein the operations further comprise:
    applying a digital signature, by the data owner device, to the record key encrypted using the data consumer public key before transmitting the record key encrypted using the data consumer public key to the data consumer.

13. The non-transitory computer-readable memory of claim 10, wherein the operations further comprise: denying access to the record, by the data owner device, based at least on a time the second request was generated or an identity of the data consumer.

14. The non-transitory computer-readable memory of claim 10, wherein the data owner is a patient and the data consumer is a medical provider.

15. The non-transitory computer-readable memory of claim 9, wherein prior to encrypting the record using the record key, the operations further comprise generating, by the data owner device, a cryptographic hash of the record.

16. The non-transitory computer-readable memory of claim 15, wherein the operations further comprise:
    providing, by the data owner device via the communications network, the cryptographic hash to the storage device for storage in association with the record key and the transaction identification.

17. A system comprising:
    a memory; and
    at least one processor coupled to the memory and configured to:
        generate a first key identifier corresponding to a first public-private key pair of a data owner, wherein the first public-private key pair comprises a first public key of the data owner and a first private key of the data owner;
        generate a second key identifier corresponding to a second public-private key pair of the data owner, wherein the second public-private key pair comprises a second public key of the data owner and a second private key of the data owner;
        receive, via a communications network, a record comprising data of the data owner, wherein the record is encrypted using the first public key of the data owner;
        decrypt the record using the first private key of the data owner;
        generate a record key;
        encrypt the record using the record key;
        encrypt the record key using the first private key of the data owner;
        provide, via the communications network, the encrypted record key and the first key identifier to a storage device for storage, wherein the storage device is remote from the system;
        receive, via the communications network, a transaction identification corresponding to the encrypted record key and the first key identifier, wherein the transaction identification is generated when the encrypted record key and the first key identifier are stored on the storage device;
        provide, via the communications network, the record encrypted with the record key to a data intermediary for storage at the data intermediary, wherein the data intermediary is remote from the system and the storage device;
        receive, via the communications network, a request from a data consumer to access the record, wherein the request comprises at least the transaction identification and the request is encrypted with the second public key of the data owner;
        decrypt the request using the second private key of the data owner;
        retrieve, from the storage device via the communications network, the encrypted record key corresponding to the transaction identification;
        decrypt the encrypted record key using the first private key, wherein the first private key is identified based on the first key identifier associated with the transaction identification;
        encrypt the record key using a public key of the data consumer; and
        transmit, via the communications network, the record key encrypted using the public key of the data consumer to a data consumer device.

18. The system of claim 17, the at least one processor further configured to:
    receive, via the communications network, a second request to access the record from the data consumer device, wherein the second request comprises the transaction identification and the second request is encrypted with the first public key of the data owner;
    decrypt the second request to obtain the transaction identification using the first private key; and
    retrieve, from the storage device via the communications network, the encrypted record key corresponding to the transaction identification.

19. The system of claim 18, the at least one processor further configured to:
    decrypt the encrypted record key using the first private key, wherein the first private key is identified based on the first key identifier;
    encrypt the record key using the public key of the data consumer; and
    transmit, via the communications network, the record key encrypted using the public key of the data consumer to the data consumer.

20. The system of claim 19, the at least one processor further configured to:
    apply a digital signature to the record key encrypted using the data consumer public key before transmitting the record key encrypted using the data consumer public key to the data consumer.

21. The system of claim 18, the at least one processor further configured to:
    deny access to the record based at least on a time the second request was generated or an identity of the data consumer.

22. The system of claim 18, wherein the data owner is a patient and the data consumer is a medical provider.

23. The system of claim 17, wherein prior to encrypting the record using the record key, the at least one processor further configured to: generate, by the data owner device, a cryptographic hash of the record.

24. The system of claim 23, the at least one processor further configured to:
provide, via the communications network, the cryptographic hash to the storage device for storage in association with the record key and the transaction identification.

* * * * *

UNITED STATES PATENT AND TRADEMARK OFFICE
CERTIFICATE OF CORRECTION

| | | |
|---|---|---|
| PATENT NO. | : 12,395,329 B1 | Page 1 of 1 |
| APPLICATION NO. | : 18/759426 | |
| DATED | : August 19, 2025 | |
| INVENTOR(S) | : Pasquali et al. | |

It is certified that error appears in the above-identified patent and that said Letters Patent is hereby corrected as shown below:

In the Claims

In Column 31, Claim 8, Line 54, delete "the the" and insert -- the --, therefor.

In Column 32, Claim 9, Line 4, delete "at the" and insert -- the --, therefor.

In Column 33, Claim 12, Line 12, delete "memory" and insert -- memory of --, therefor.

In Column 34, Claim 18, Line 35, delete "owner," and insert -- owner; --, therefor.

Signed and Sealed this
Fourteenth Day of October, 2025

John A. Squires
*Director of the United States Patent and Trademark Office*